United States Patent
Greenwald et al.

(10) Patent No.: US 6,180,095 B1
(45) Date of Patent: Jan. 30, 2001

(54) POLYMERIC PRODRUGS OF AMINO- AND HYDROXYL-CONTAINING BIOACTIVE AGENTS

(75) Inventors: Richard B. Greenwald, Somerset; Annapurna Pendri, Matawan; Yun H. Choe, Piscataway, all of NJ (US)

(73) Assignee: Enzon, Inc., Piscataway, NJ (US)

( * ) Notice: Under 35 U.S.C. 154(b), the term of this patent shall be extended for 0 days.

(21) Appl. No.: 09/183,557

(22) Filed: Oct. 30, 1998

Related U.S. Application Data

(63) Continuation-in-part of application No. 08/992,435, filed on Dec. 17, 1997, now abandoned.

(51) Int. Cl.[7] .................. A61K 31/21; A61K 31/704; A61K 31/765; A61K 38/02; A61K 31/33

(52) U.S. Cl. .................. 424/85.1; 424/85.2; 424/85.4; 424/94.3; 435/188; 514/2; 514/13; 514/18; 514/34; 514/49; 514/247; 514/345; 514/351; 514/352; 514/424; 514/425; 514/426; 514/432; 514/445; 514/447; 514/459; 514/460; 514/471; 514/472; 514/473; 514/480; 514/512; 514/547; 530/326; 530/330; 530/345; 530/351; 530/408; 530/409; 530/410; 536/6.4; 536/28.5

(58) Field of Search .................. 526/332; 528/421; 536/4.1, 6.4, 16.8, 17.2, 18.1, 28.5; 514/34, 49, 247, 345, 351, 352, 424, 425, 426, 432, 445, 447, 459, 460, 471, 472, 473, 480, 512, 547, 2, 13, 18; 424/85.1, 85.2, 85.4, 94.3; 530/326, 330, 345, 351, 408, 409, 410; 435/188

(56) References Cited

U.S. PATENT DOCUMENTS

| | | | |
|---|---|---|---|
| 4,179,337 | 12/1979 | Davis et al. | 435/181 |
| 5,093,531 | 3/1992 | Sano et al. | 568/337 |
| 5,122,614 | 6/1992 | Zalipsky | 548/520 |
| 5,321,095 | 6/1994 | Greenwald | 525/404 |
| 5,349,001 | 9/1994 | Greenwald et al. | 525/408 |
| 5,382,657 | * 1/1995 | Karasiewicz et al. | 530/351 |
| 5,561,119 | 10/1996 | Jacquesy et al. | 514/34 |
| 5,605,976 | 2/1997 | Martinez et al. | 525/408 |
| 5,614,549 | * 3/1997 | Greenwald et al. | 514/449 |
| 5,643,575 | 7/1997 | Martinez et al. | 424/194.1 |
| 5,672,584 | 9/1997 | Borchardt et al. | 514/11 |
| 5,710,135 | 1/1998 | Leenders et al. | 514/34 |
| 5,840,900 | * 11/1998 | Greenwald et al. | 546/48 |
| 5,965,119 | * 10/1999 | Greenwald et al. | 424/78.37 |

FOREIGN PATENT DOCUMENTS

WO/98/13059   4/1998   (WO).

OTHER PUBLICATIONS

Zier et al, Polyethylene Glycol Bound Benzyl–And Fluorenyl Derivatives . . . Tetrahedron Letters, vol. 35, No. 7, pp. 1039–1042, 1994.*

Carl, P.L., et al. A Novel Connector Linkage Applicable in Prodrug Design, Journal of Medicinal Chemistry, vol. 24, No. 5 (May 1981).

Shan, D., et al., Prodrug Strategies Based on Intramolecular Cyclization Reactions, Journal of Pharmaceutical Sciences, Jul. 1997, vol. 86, No. 7, pp765–767.

Shearwater Polymers, Inc., Catalog—Polyethylene Glycol Derivatives, 1997–1998; p. 8.

Leenders, R.G.G. et al., Highly Diastereoselective Synthesis of Anomeric B–O–Glycopyranosyl Carbamates from Isocyanates, Synthesis Nov. 1996; pp. 1309–1312.

Record of Invention "2–and 4–Hydroxybenzyl Alcohol–Containing Linkers", Zalipsky, Nov. 18, 1991.

Declaration under 37 C.F.R. 1.132 of Richard B. Greenwald including Exhibits 1 and 2, Sep. 8, 1999.

Declaration under 37 C.F.R. 1.132 of Jeffrey McGuire, Sep. 8, 1999.

Leenders, R.G.G. et al, B–Glucuronyl Carbamate Based Pro–moieties Designed for Prodrugs in ADEPT, 1995; Tetrahedron Letters vol. 36, No. 10 pp. 1701–1704.

Waldmann, H. et al, Synthesis of the Palmitoylated and Farnesylated C–Terminal Lipohexapeptide of the Human N–Ras Protein by Employing . . . , Angew. Chem Int. Ed. 1995, 34 No.20 ; pp. 2259–2262.

Jungheim, L.N. et al., Design of Antitumor Prodrugs: Substrates for Antibody Targeted Enzymes, Chem. Rev. 1994; 94 pp. 1553–1566.

Bundgaard, H. The Double Prodrug Concept and its Applications, Advanced Drug Delivery Reviews, 3 1989 pp. 39–65.

Wakselman, M. et al., An Alkali–labile Substituted Benzyloxycarbonyl Amino–protecting Group, JCS Chem. Comm1973; pp. 593–594.

* cited by examiner

*Primary Examiner*—Jeffrey E. Russel
(74) *Attorney, Agent, or Firm*—Roberts & Mercanti LLP

(57) ABSTRACT

The present invention is directed to double prodrugs containing polymeric-based transport forms. These polymeric prodrugs are preferably of the formula:

(I)

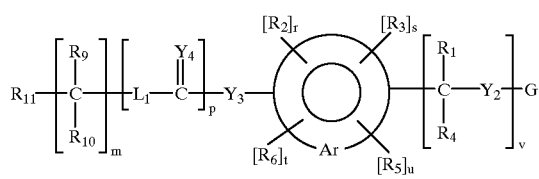

wherein:

$L_1$ is a bifunctional linking moiety;

G is H or

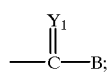

where

B is H, a leaving group, a residue of an amine-containing moiety, or a residue of a hydroxyl-containing moiety;

$Y_{1-4}$ are independently, O, S, or $NR_{12}$;

$R_1$, $R_4$, $R_9$, $R_{10}$, and $R_{12}$, are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls;

$R_2$, $R_3$, $R_5$ and $R_6$ are independently selected from the group consisting of hydrogen, $C_{1-6}$ alkyls, $C_{1-6}$ alkoxy, phenoxy, $C_{1-8}$ heteroalkyls, $C_{1-8}$ heteroalkoxy, substituted $C_{1-6}$ alkyls, $C_{3-8}$ cycloalkyls, $C_{3-8}$ substituted cycloalkyls, aryls, substituted aryls, aralkyls, halo-, nitro-, cyano-, carboxy-, $C_{1-6}$ carboxyalkyls and $C_{1-6}$ alkyl carbonyls;

Ar is a moiety which when included in Formula (I) forms a multi-substituted aromatic hydrocarbon or a multi-substituted heterocyclic group;

(m), (r), (s), (t), (u) and (v) are independently zero or one;

(p) is zero or a positive integer; and $R_{11}$ is a substantially non-antigenic polymer.

The first prodrug is generated when the polymeric portion of the double prodrug is cleaved and the parent molecule is generated rapidly thereafter in vivo, preferably as a result of 1,6 or 1,4 benzyl elimination-reaction. Methods of preparing the compounds and methods of treatment are also disclosed.

56 Claims, 6 Drawing Sheets

POLYMERIC PRODRUGS OF AMINO- AND HYDROXYL-CONTAINING BIOACTIVE AGENTS

CROSS REFERENCE TO RELATED APPLICATIONS

This application is a continuation-in-part of U.S. patent application Ser. No. 08/992,435 filed Dec. 17, 1997, now abandoned, the contents of which are incorporated herein by reference.

TECHNICAL FIELD

The present invention relates to double prodrugs. In particular, the invention relates to polymeric-based double prodrugs having reversible linkages involving amino and hydroxyl moieties of chemical compounds and biologically active materials such as enzymes, proteins and the like.

BACKGROUND OF THE INVENTION

Over the years, several methods of administering biologically-effective materials to mammals have been proposed. Many medicinal agents are available as water-soluble salts and can be included in pharmaceutical formulations relatively easily. Problems arise when the desired medicinal agent is either insoluble in aqueous finds or is rapidly degraded in vivo. For example, alkaloids are often especially difficult to solubilize.

One way to solubilize medicinal agents is to include them as part of a soluble prodrug. Prodrugs include chemical derivatives of a biologically-active parent compound which, upon administration, eventually liberate the parent compound in vivo. Prodrugs allow the artisan to modify the onset and/or duration of action of an agent in vivo and can modify the transportation, distribution or solubility of a drug in the body. Furthermore, prodrug formulations often reduce the toxicity and/or otherwise overcome difficulties encountered when administering pharmaceutical preparations. Typical examples of prodrugs include organic phosphates or esters of alcohols or thioalcohols. See *Remington's Pharmaceutical Sciences,* 16th Ed., A. Osol, Ed. (1980), the disclosure of which is incorporated by reference herein.

Prodrugs are often biologically inert, or substantially inactive, forms of the parent or active compound. The rate of release of the active drug, i.e. the rate of hydrolysis, is influenced by several factors but especially by the type of bond joining the parent drug to the modifier. Care must be taken to avoid preparing prodrugs which are eliminated through the kidney or reticular endothelial system, etc. before a sufficient amount of hydrolysis of the parent compound occurs. By incorporating a polymer as part of the prodrug system, one can increase the circulating half-life of the drug. However, in some situations such as with alkaloids, it has been determined that when only one or two polymers of less than about 10,000 daltons are conjugated thereto, the resulting conjugates are rapidly eliminated in vivo especially if a somewhat hydrolysis-resistant linkage is used. In fact, such conjugates are so rapidly cleared from the body that even if a hydrolysis-prone ester linkage is used, not enough of the parent molecule is regenerated in vivo. This is often not a concern with moieties such as proteins, enzymes and the like even when hydrolysis-resistant linkages are used. In those cases multiple polymer strands, each having a molecular weight of about 2–5 kDa, are used to further increase the molecular weight and circulating half-life.

Although the above-mentioned concept of prodrug-based delivery systems has proven to be useful in many instances, there are nonetheless situations where alternatives are desired. For example, Bundgaard in "The Double Prodrug Concept and Its Applications" in *Advanced Drug Delivery Reviews,* 3 (1989) 39–65, (the contents of which are hereby incorporated by reference) pointed out that in many cases it is difficult to obtain a prodrug which has the proper combination of adequate stability in vitro and high susceptibility to regenerate the parent drug in vivo. As pointed out by Bundgaard, a promising means of overcoming some of the previously encountered shortcomings involves the use of cascade latentiation or "pro-prodrugs". In such systems, the hydrolytic reaction sequence involves a first step which usually is an enzymatic cleavage and the second involves a non-enzymatic hydrolysis that occurs only after the first has taken place.

it is believed that in spite of the reported work in the field of double prodrugs, some specific problems were not addressed sufficiently. For example, the previously reported techniques do not sufficiently address the solubility problems of many parent compounds. In addition, the problem of designing in a sufficient increase in circulating half-life for the prodrug was also not sufficiently developed. Thus, there continues to be a need to provide additional technologies for forming prodrugs which would benefit from the double prodrug concept. For example, it would be advantageous to provide the artisan with alternative techniques for transport carrier attachment so as to regulate biological effect. Furthermore, it would be desirable to provide additional techniques to address problems associated with involving amino residues of parent compounds and thus avoid excessively fast or slow hydrolysis of the transport form from the parent compound at physiological pH.

SUMMARY OF THE INVENTION

The present invention addresses the shortcomings described above. In one aspect of the invention, compounds of Formula (I) are provided:

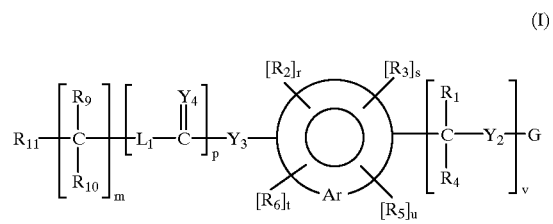

wherein:

$L_1$ is a bifunctional linking moiety such as

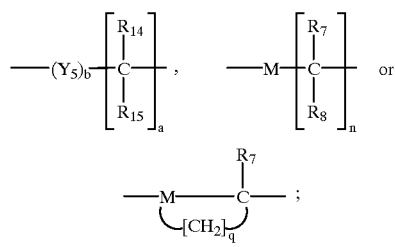

G is H or

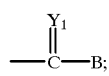

where
B is H, a leaving group, a residue of an amine-containing moiety, or a residue of a hydroxyl-containing moiety;
$Y_{1-5}$ are independently O, S or $NR_{12}$;
M is X or Q; wherein
X is an electron withdrawing group
Q is a moiety containing a free electron pair positioned three to six atoms from

$R_1$, $R_4$, $R_7$, $R_8$, $R_9$, $R_{10}$, $R_{12}$, $R_{14}$ and $R_{15}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls;
$R_2$, $R_3$, $R_5$ and $R_6$ are independently selected from the group consisting of hydrogen, $C_{1-6}$ alkyls, $C_{1-6}$ alkoxy, phenoxy, $C_{1-8}$ heteroalkyls, $C_{1-8}$ heteroalkoxy, substituted $C_{1-6}$ alkyls, $C_{3-8}$ cycloalkyls, $C_{3-8}$ substituted cycloalkyls, aryls, substituted aryls, aralkyls, halo-, nitro- and cyano-, carboxy-, carboxyalkyl, alkylcarbonyl, etc.;
Ar is a moiety which when included in Formula (I) forms a multi-substituted aromatic hydrocarbon or a multi-substituted heterocyclic group;
(b), (m), (r), (s), (t), (u), and (v) are independently zero or one;
(a) and (n) are independently zero or a positive integer;
(p) is zero or a positive integer;
(q) is three or four; and
$R_{11}$ is a polymer such as a polyalkylene oxide.
In some preferred embodiments, (r) and (t) are one and $R_2$ and $R_6$ are independently selected from $C_{1-6}$ alkoxy or $C_{1-6}$ alkyl moieties and $R_3$ and $R_5$ are both hydrogen.
In other preferred embodiments, (v) is zero,

where B is hydrogen. This aldehyde derivative of Formula (I) provides useful intermediates for forming prodrug compositions.
In alternative preferred aspects of the invention, B is a leaving group such as N-hydroxy-benzotriazolyl, N-hydroxyphthalimidyl, halogen, p-nitrophenoxy, imidazolyl, N-hydroxysuccinimidyl, thiazolidyl thione, or other activating groups. Alternatively, B is a residue of any amino-containing or hydroxyl-containing compound for which one or more of improved aqueous solubility, decreased antigenicity, prodrug and/or controlled release delivery is desired. For example, B, can be a residue of an enzyme, protein, or organic compound such as daunorcubicin, doxorubicin, p-aminoaniline mustard, camptothecin, paclitaxel, Ara-C, melphalan, podophyllotoxin, etc.

For purposes of the present invention, the term "residue" shall be understood to mean that portion of a biologically active compound which remains after it has undergone a substitution reaction in which the prodrug carrier portion has been attached.

For purposes of the present invention, the term "alkyl" shall be understood to include straight, branched, substituted $C_{1-12}$ alkyls, $C_{3-8}$ cycloalkyls or substituted cycloalkyls, etc.

The double prodrugs of the present invention are thus unique delivery systems. Preferably the polymeric portion is first released by hydrolysis and then the result "second prodrug" moiety undergoes a 1,4 or 1,6-aryl or benzyl elimination reaction to regenerate the amine-containing bioactive compound.

Some of the chief advantages of the double prodrug compounds of the present invention are that they are capable of solubilizing amine-containing or hydroxyl-containing compounds and extending their half-life as compared to the native or even "second" prodrug counterparts. The linkage between the polymer and the "second prodrug" compound as described above, hydrolyzes at a rate which allows the compound to retain its enhanced solubility and circulating half-life. The native drug, however, is still not released at this point. Only after the "second prodrug" undergoes 1,4 or 1,6-benzyl elimination, will the desired native molecule be released. It is readily apparent that this double prodrug approach of the present invention offers unique and unexpected characteristics which enhance the circulating half-life and solubility of native molecules.

Methods of making and using the compounds and conjugates described herein are also provided.

DETAILED DESCRIPTION OF THE INVENTION

Figure 1:
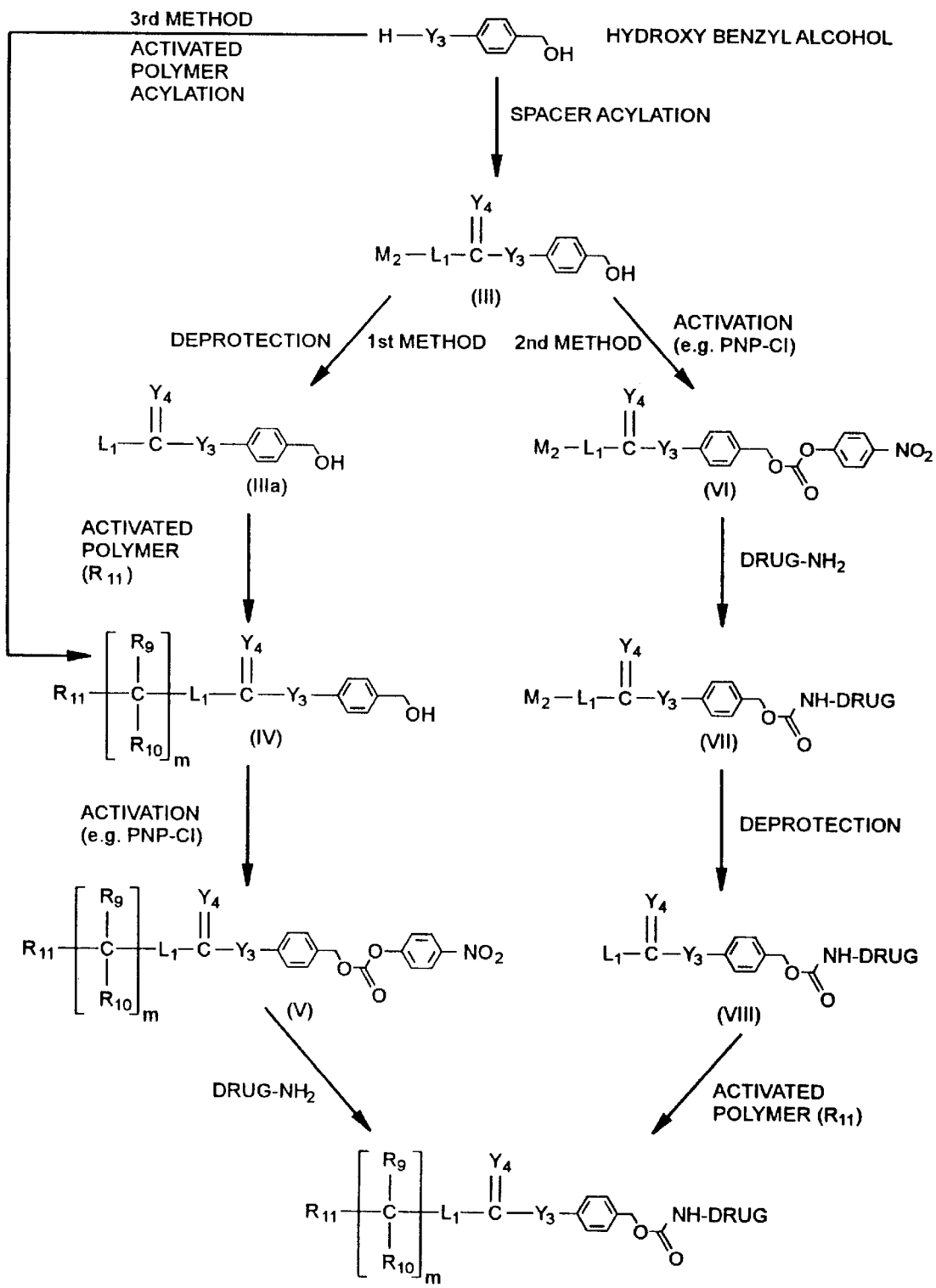
FIG. 1 depicts the three synthetic methods for making the polymeric double prodrugs of the present invention.
Figure 2:
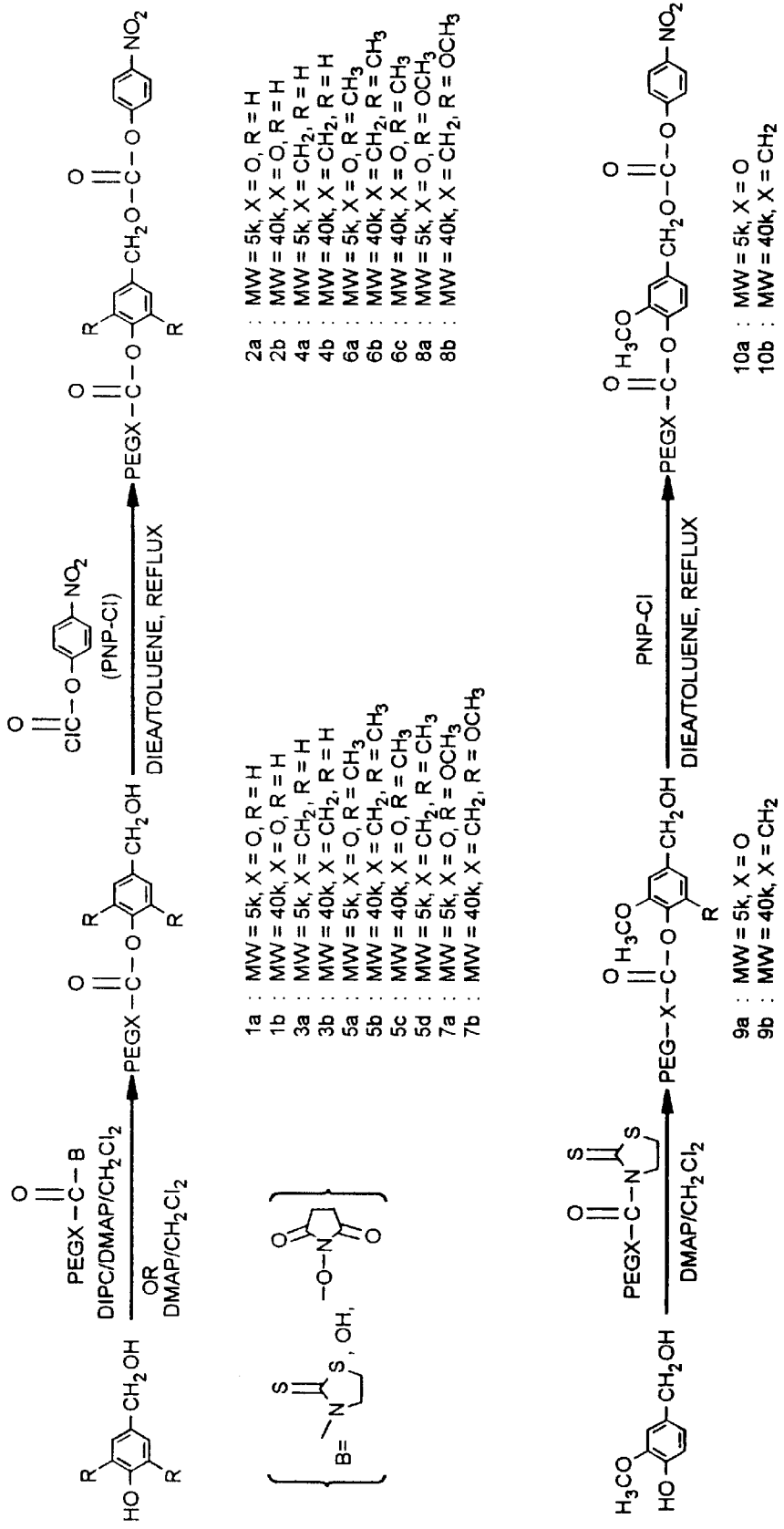
FIG. 2 illustrates reaction schemes to prepare compounds 1a through 10b.
Figure 3:
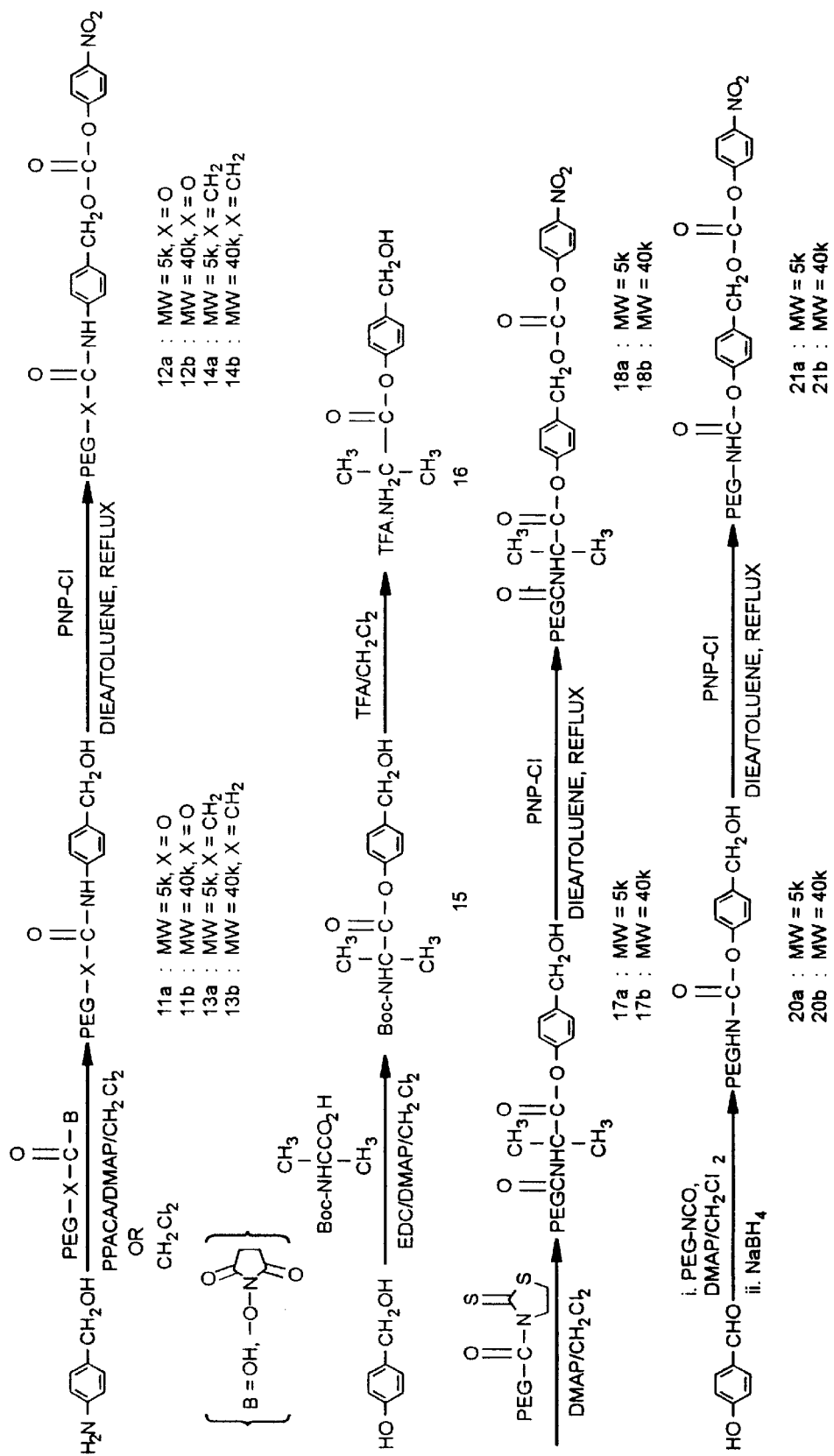
FIG. 3 illustrates reaction schemes to prepare compounds 11a through 21b.
Figure 4:
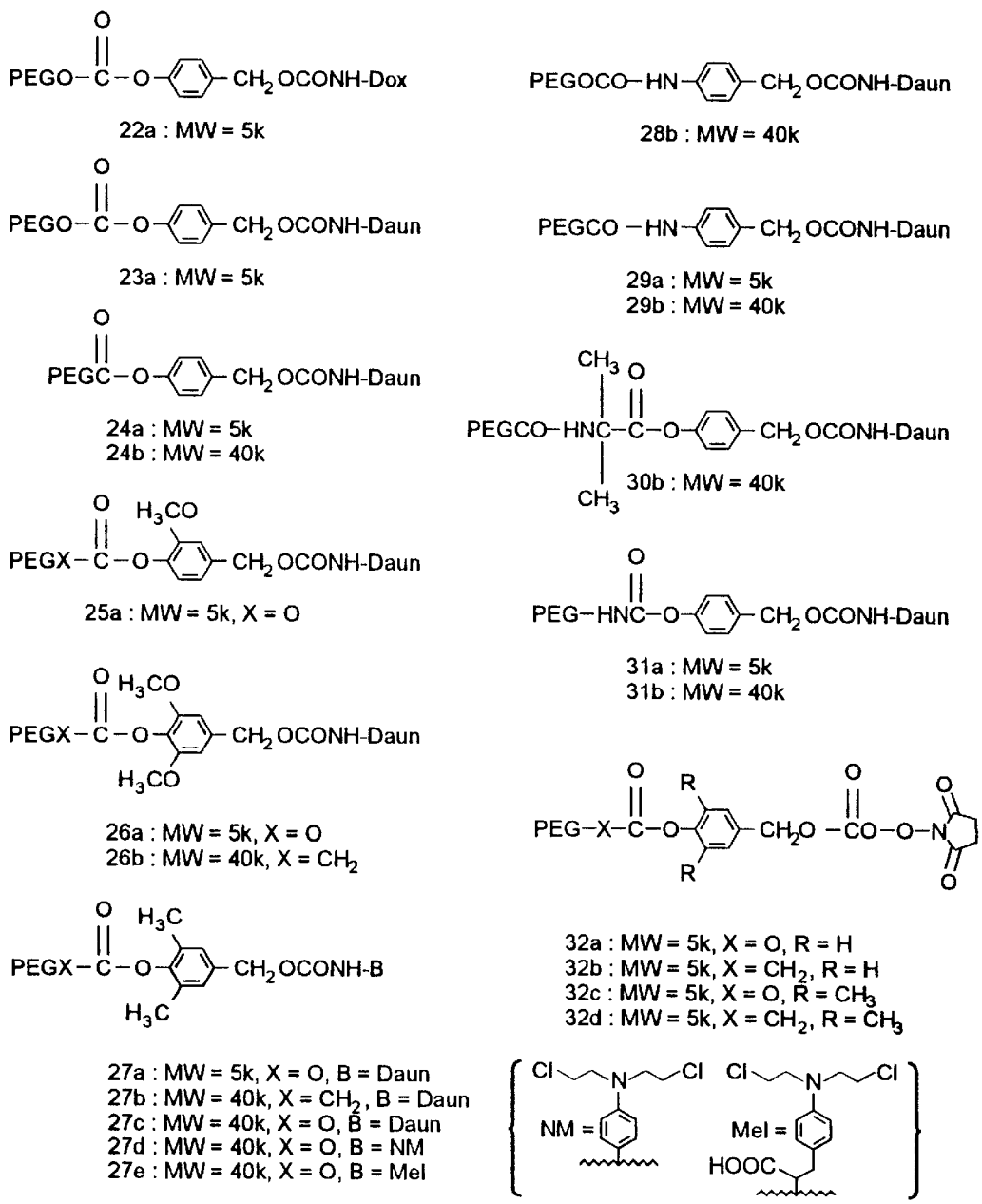
FIG. 4 illustrates reaction schemes to prepare compounds 22a through 32d.
Figure 5:
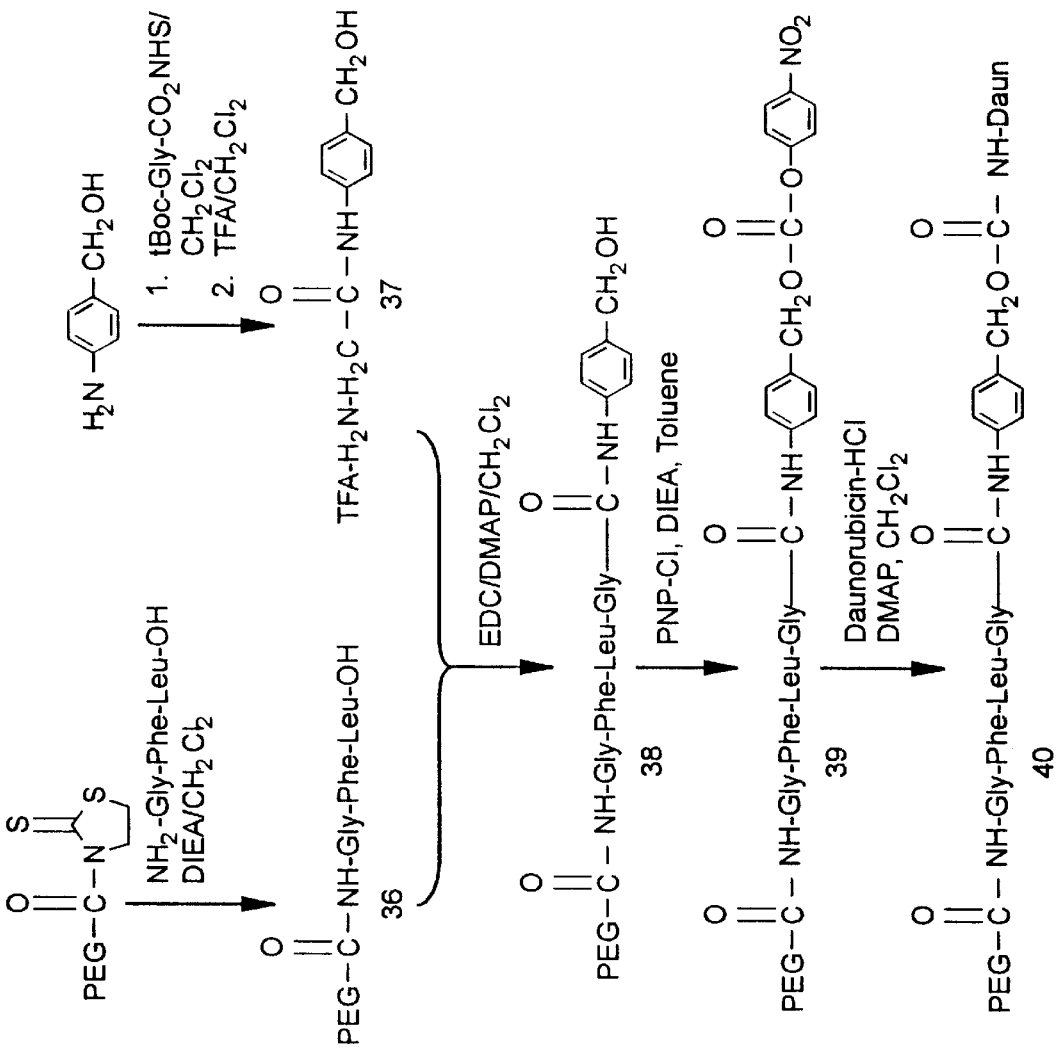
FIG. 5 illustrates reaction schemes to prepare compounds 36 through 40. In addition, the amino acid residues of SEQ ID NO:1 are present in reaction products numbered as 39 and 40 in this figure.
Figure 6:
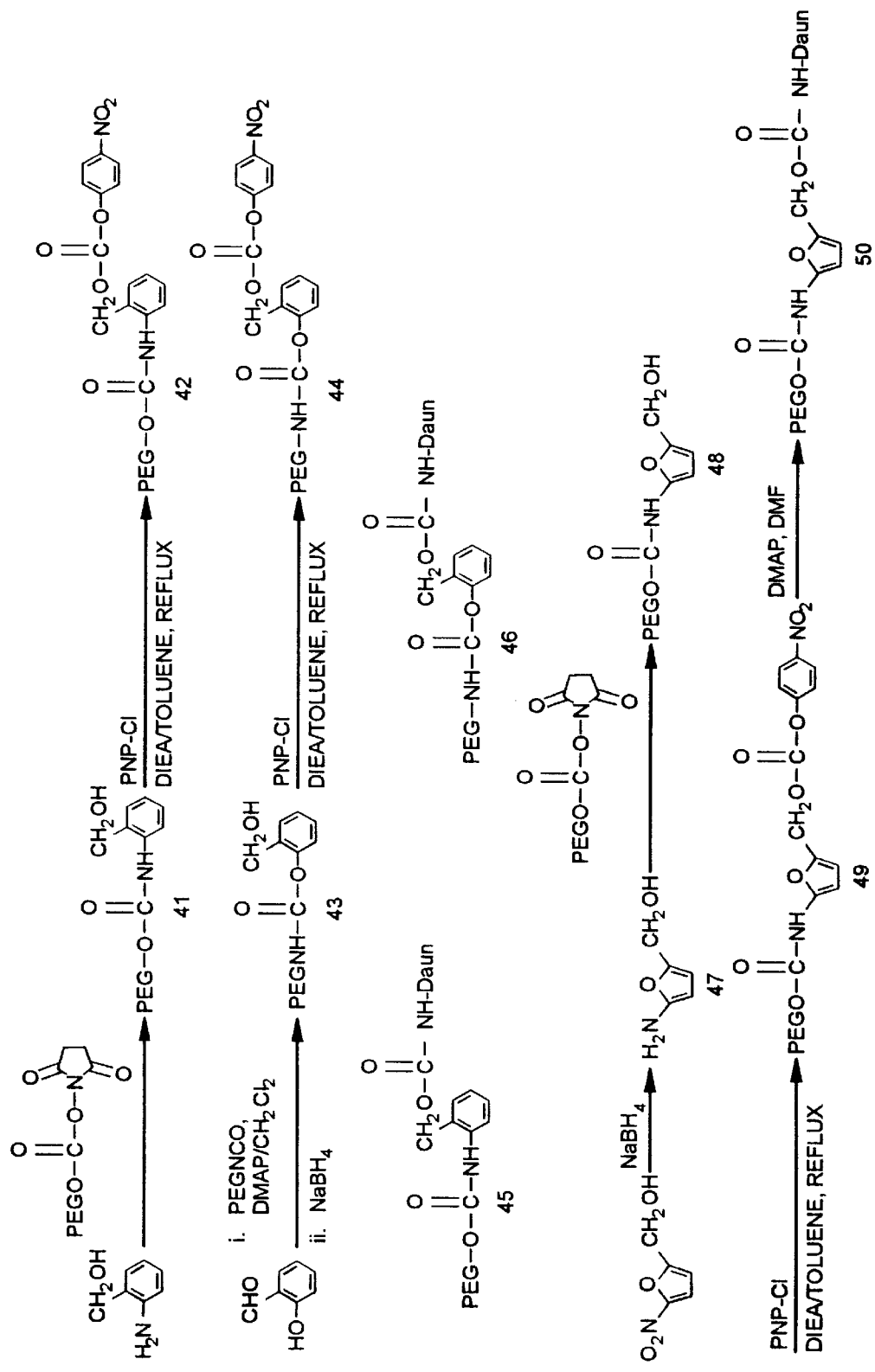
FIG. 6 illustrates reaction schemes to prepare compounds 41 through 50.

A. Formula (I)
In one aspect of the invention, there are provided compounds of formula (I):

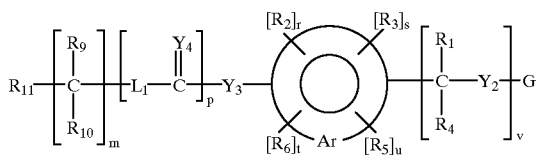
(I)

wherein:

$L_1$ is a bifunctional linking moiety such as

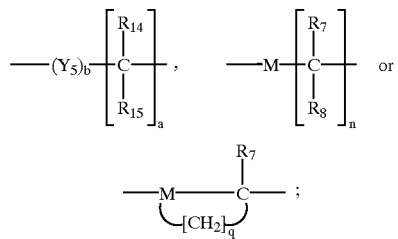

G is H or

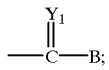

where

B is H, a leaving group, a residue of an amine-containing moiety, or a residue of a hydroxyl-containing moiety;

$Y_{1-5}$ are independently O, S or $NR_{12}$;

M is X or Q; where

X is an electron withdrawing group;

Q is a moiety containing a free electron pair positioned three to six atoms from

$R_1$, $R_4$, $R_7$, $R_8$, $R_9$, $R_{10}$, $R_{12}$, $R_{14}$ and $R_{15}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls;

$R_2$, $R_3$, $R_5$ and $R_6$ are independently selected from the group consisting of hydrogen, $C_{1-6}$ alkyls, $C_{1-6}$ alkoxy, phenoxy, $C_{1-8}$ heteroalkyls, $C_{1-8}$ heteroalkoxy, substituted $C_{1-6}$ alkyls, $C_{3-8}$ cycloalkyls, $C_{3-8}$ substituted cycloalkyls, aryls, substituted aryls, aralkyls, halo-, nitro- and cyano-, carboxy-, carboxyalkyl, alkylcarbonyl, etc.;

Ar is a moiety, which when included in Formula (I), forms a multi-substituted aromatic hydrocarbon or a multi-substituted heterocyclic group;

(b), (m), (r), (s), (t), (u) and (v) are independently zero or one;

(a) and (n) are independently zero or a positive integer, preferably 1–6 inclusive;

(p) is zero or a positive integer, preferably 1–6 inclusive;

(q) is three or four; and $R_{11}$ is a substantially non-antigenic polymer.

B. Description of the Ar Moiety

Referring to Formula (I), it can be seen that the Ar moiety is a moiety which when included in Formula (I) forms a multi-substituted aromatic hydrocarbon or a multi-substituted heterocyclic group. A key feature is that the Ar moiety is aromatic in nature. Generally, to be aromatic, the π electrons must be shared within a "cloud" both above and below the plane of a cyclic molecule. Furthermore, the number of π electrons must satisfy the Hückle rule (4n+2). Those of ordinary skill will realize that a myriad of moieties will satisfy the aromatic requirement of the moiety and thus are suitable for use herein.

Preferred aromatic hydrocarbon moieties include, without limitation:

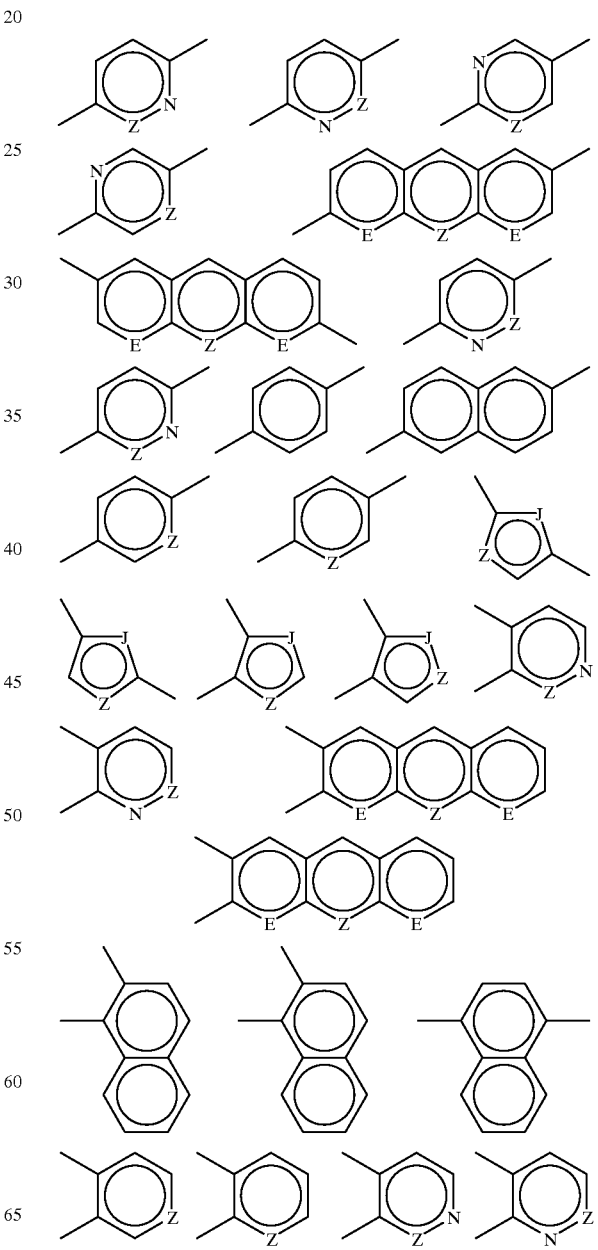

-continued

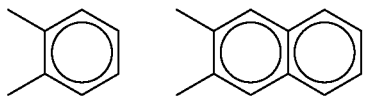

wherein J is O, S, or $NR_{13}$, E and Z are independently $CR_{13}$ or $NR_{13}$; and $R_{13}$ is independently selected from the same group as that which defines $R_9$ in Formula (I) e.g. hydrogen, $C_{1-6}$ alkyls, etc. Isomers of the five and six-membered rings are also contemplated as well as benzo- and dibenzo- systems and their related congeners are also contemplated. It will also be appreciated by the artisan of ordinary skill that the aromatic rings can optionally be substituted with heteroatoms such as O, S, $NR_{13}$, etc. so long as Hückel's rule is obeyed. Furthermore, the aromatic or heterocyclic structures may optionally be substituted with halogen(s) and/or side chains as those terms are commonly understood in the art. However, all structures suitable for Ar moieties of the present invention are capable of allowing the $Y_3$ and $C(R_1)(R_4)$ moieties to be in a para or an ortho arrangement with the same plane as shown:

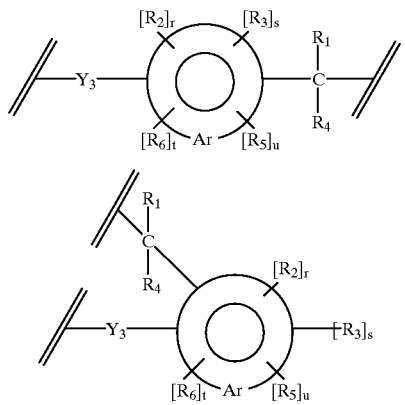

where all variables are as defined above with regard to Formula (I).

When the Ar moiety includes a para arrangement of the $Y_3$ and $C(R_1)(R_4)$ moieties, preferred aspects of the present invention define (r), (s), (t), and (u) as one and $R_2$ and $R_6$ as being independently selected from the group consisting of methyl, $C_{1-6}$ alkyls, methyl, $C_{1-6}$ alkoxys, and methoxy. More preferably, $R_2$ and $R_6$ are either both methyl or methoxy moieties. Furthermore, $R_3$ and $R_5$ are preferably both hydrogen, $R_1$ and $R_4$ are preferably either hydrogen, $CH_3$ or $CH_2CH_3$. $Y_{1-5}$ are preferably O or $NR_{12}$ where $R_{12}$ is H or a $C_{1-6}$ alkyl or substituted alkyl. More preferably, $Y_1$ and $Y_4$ are O.

For purposes of the present invention, substituted alkyls include carboxyalkyls, aminoalkyls, dialkylaminos, hydroxyalkyls and mercaptoalkyls; substituted cycloalkyls include moieties such as 4-chlorocyclohexyl; aryls include moieties such as naphthyl; substituted aryls include moieties such as 3-bromophenyl; aralkyls include moieties such as toluyl; heteroalkyls include moieties such as ethylthiophene; substituted heteroalkyls include moieties such as 3-mehtoxythiophene; alkoxy includes moieties such as methoxy; and phenoxy includes moieties such as 3- nitrophenoxy. Halo- shall be understood to include fluoro, chloro, iodo and bromo.

C. Linker Moiety $L_1$

As shown above, the invention includes bifunctional linking moiety $L_1$ which when combined with

forms an amino acid residue linker, or when (p) is greater than one, a peptide residue linker.

Suitable amino acid residues can be selected from naturally-occurring or synthetic, i.e. non-naturally-occurring, amino acids including alanine, valine, leucine, isoleucine, glycine, serine, threonine, methionine, cysteine, phenylalanine, tyrosine, tryptophan, aspartic acid, glutamic acid, lysine, arginine, histidine or proline. Some preferred peptide residues include Gly—Phe—Leu—Gly (SEQ ID NO: 1) and Gly—Phe—Leu. It is noted that the terminal amino group of the amino acid or peptide residue will be proximal to $R_{11}$ (i.e. polymer). Peptides can be readily synthesized or obtained from commercial sources for inclusion herein.

In alternative embodiments, $L_1$ includes the moiety (M) which is either an electron withdrawing group (designated herein as X), or a moiety containing a free electron pair positioned three to six atoms from the

(designated herein as Q).

D. The Double Prodrug Linkage Portion

The first labile bond of the double prodrug system, which joins the $L_1$ to

is selected to hydrolyze, such as via an esterase catalyzed hydrolysis in vivo at a rate which generates sufficient amounts of the "second" prodrug compound within a suitable time after administration. The term "sufficient amounts" for purposes of the present invention shall mean an amount which may later undergo sufficient 1,4 or 1,6-benzyl elimination in vivo to release the native compound and achieve a desired effect. Preferably, (n) is an integer from 1 to about 12. More preferably, (n) is 1 or 2.

1. The Electron Withdrawing Group X

In those aspects of Formula (I) where $L_1$ includes M, the moiety may be an electron withdrawing group, designated herein as X. For purposes of the present invention, "electron withdrawing groups" are groups which tend to pull shared electrons toward themselves thereby making carbon more electro-positive. This, in turn, destabilizes the carbonyl moiety, causing more rapid hydrolysis. Thus, when X is in the α position to the ester, it modulates the rates of hydrolysis and enzymatic cleavage. In particular, X can be moieties such as O, $NR_{12}$,

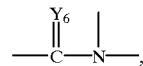

S, SO and $SO_2$ where $Y_6$ is the same as that defined by $Y_1$ and $R_{12}$ is defined above, i.e. H, $C_{1-6}$ alkyls, branched alkyls, aryls, etc. Preferably, however, when X is $NR_{12}$, $R_{12}$ is H, a $C_{1-6}$ alkyl such as methyl or ethyl or substituted $C_{1-6}$ alkyl. It is preferred that X is either O or $NR_{12}$.

2. Q Portion of the Linker

Alternatively, when $L_1$ includes Q, which is a moiety containing a free electron pair positioned three to six atoms from the

moiety, the polymer, $R_{11}$, is preferably attached to Q via a heteroatom such as oxygen. In a preferred embodiment, the free electron pair is five atoms from this oxygen, Q can be selected from the non-limiting list of $C_{2-4}$ alkyls or cycloalkyls, aryls or aralkyl groups substituted with a member of the group consisting of O, S and $NR_{12}$. The free electron pair can be anywhere along the Q moiety as long as the defined spacing between th free electron pair and $Y_4$ is maintained.

In these embodiments, $R_{11}$ is attached to Q via $NR_{12}$, O, or S. Thus, Q assists hydrolysis of the prodrug linkage by anchimeric assistance because the free electron pair moiety can generate a three- to six-membered, but preferably five-

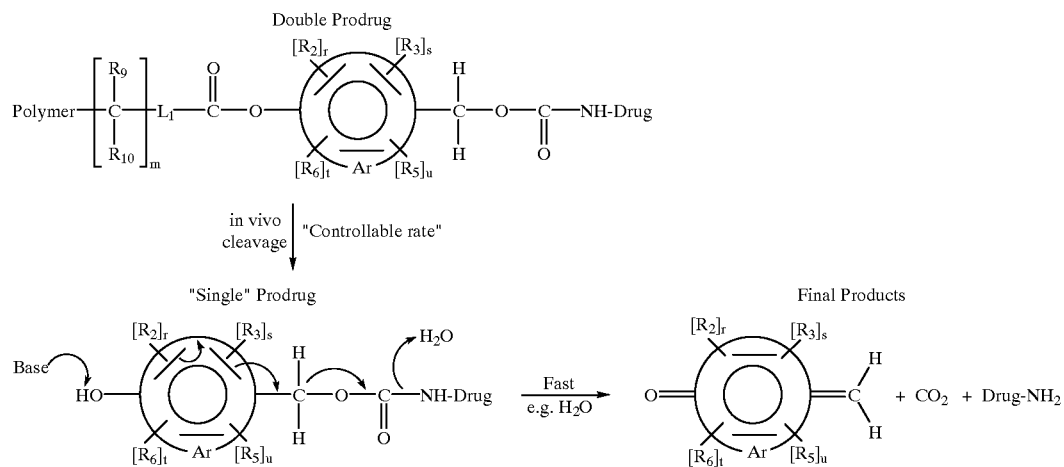

membered, ring by-product upon hydrolysis of the preferably ester linkage.

Q can also be selected from the group consisting of $C_{2-4}$ alkyls, cycloalkyls, aryls, aralkyl groups substituted with a member of the group consisting of NH, O, S, —$CH_2$—C(O)—N(H)—, and ortho-substituted phenyls such as

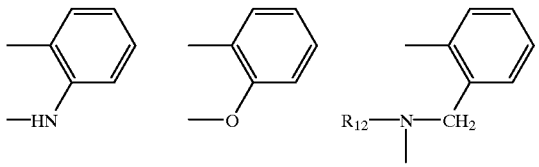

3. Drug Generation Via Hydrolysis of the Prodrug

The prodrug compounds of the present invention are designed so that the $t_{1/2}$ of hydrolysis is $<t_{1/2}$ elimination in plasma.

The linkages included in the compounds have hydrolysis rates in the plasma of the mammal being treated with is short enough to allow sufficient amounts of the parent compounds, i.e. the amino- or hydroxyl-containing bioactive compound, to be released prior to elimination. Some preferred compounds of the present invention, i.e. those in which (n) is 1, have a $t_{1/2}$ for hydrolysis in plasma ranging from about 5 minutes to 12 hours. Preferably, the compositions have a plasma $t_{1/2}$ hydrolysis ranging from about 0.5 to about 8 hours and most preferably from about 1 to about 6 hours.

4. 1,4 or 1,6-Benzyl and Native Drug Regeneration

Once the hydrolysis of the double prodrug has taken the place in vivo, usually via esterase activity or pH moderated activity or cyclization reaction, the polymeric residue is cleaved and the resultant second prodrug moiety remains. According to the present invention, this prodrug entity will undergo a further step of a 1,4 or 1,6-benzyl elimination in vivo to produce the desired native compound by electron migration causing the following irreversible decomposition which regenerates the drug. For example, when the $Y_3$ and $C(R_1)(R_4)$ moieties of the double prodrugs of the present invention for a para arrangement, a representative reaction is shown below with $Y_2$, $Y_3$, and $Y_4$ being O; $R_1$ and $R_4$ being H; and G being C(O)—B where B is a residue of an amine-containing target moiety (i.e. $NH_2$-Drug).

Although not shown, when the $Y_3$ and $C(R_1)(R_4)$ of the double prodrugs of the present invention are in an ortho arrangement, the reaction proceeds in a similar manner.

Substantially Non-Antigenic Polymers

The "double prodrug" compositions of the present invention include a water-soluble polymer, $R_{11}$.

In preferred aspects of the invention, $R_{11}$ includes a capping group A which can be hydrogen, $C_{1-6}$ alkyl moieties, carboxyalkyl, dialkyl acyl urea alkyls, or a compound of formula (II) shown below which forms a bis-system.

(II)

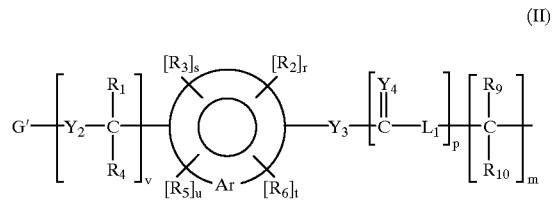

wherein G' is the same as G or another member of the group defined by G and the remaining variables are as set forth above with regard to Formula (I).

Suitable examples of such polymers include polyalkylene oxides such as polyethylene glycols which are also preferably substantially non-antigenic. The general formula for PEG and its derivatives, i.e. A'—O—(CH$_2$CH$_2$O)$_x$—(CH$_2$)$_n$—A, where (x) represents the degree of polymerization (i.e. 10–2,300) or number of repeating units in the polymer chain and is dependent on the molecular weight of the polymer; (n) is zero or a positive integer; A is a capping group as defined herein, i.e. an —H, amino, carboxy, halo, C$_{1-6}$ alkyl or other activating group and A' is the same as A or another A moiety. Also useful as polypropylene glycols, branched PEG derivatives such as those described in commonly-assigned U.S. Pat. No. 5,643,575, "star-PEG's" and multi-armed PEG's such as those described in Shearwater Polymers, Inc. catalog "Polyethylene Glycol Derivatives 1997–1998", the disclosure of each is incorporated herein by reference. It will be understood that the water-soluble polymer will be functionalized for attachment to the linkage via M, X or Q herein. As an example, the PEG portion of the produgs can be the following non-limiting compounds: —C(=Y)—(CH$_2$)$_n$—O—(CH$_2$CH$_2$O)$_x$—A, —C(=Y)—Y—(CH$_2$)$_n$—O—(CH$_2$CH$_2$O)$_x$—A and —C(=Y)—NR$_{12}$—(CH$_2$)$_n$—O—(CH$_2$CH$_2$O)$_x$—A, where Y is O or S and A, R$_{12}$, (n) and (X) are as defined above.

In many aspects of the present invention, polyethylene glycols (PEG's), mono-activated, C$_{1-4}$ alkyl-terminated PAO's such as mono-methyl-terminated polyethylene glycols (mPEG's) are preferred when mono-substituted polymers are desired; bis-activated polyethylene oxides are preferred when di-substituted prodrugs are desired.

In order to provide the desired hydrolyzable linkage, mono- or di-acid activated polymers such as PEG acids or PEG diacids can be used as well as mono- or di-PEG amines and mono- or di-PEG diols. Suitable PAO acids can be synthesized by first converting mPEG—OH to an ethyl ester followed by saponification. See also Gehrhardt, H., et al. *Polymer Bulletin* 18:487 (1987) and Veronese, F. M., et al., *J. Controlled Release* 10; 145 (1989). Alternatively, the PAO-acid can be synthesized by converting mPEG—OH into a t-butyl ester followed by acid cleavage. See, for example, commonly assigned U.S. Pat. No. 5,605,976. The disclosures of each of the foregoing are incorporated by reference herein.

Although PAO's and PEG's can vary substantially in number average molecular weight, polymers ranging from about 2,000 to about 100,000 daltons are usually selected for the purposes of the present invention. Molecular weights of from about 5,000 to about 50,000 are preferred and 5,000 to about 40,000 are particularly preferred. The number average molecular weight of the polymer selected for inclusion in the "double prodrug" must be sufficient so as to provide sufficient circulation of the "double prodrug" before hydrolysis of the linker. Within the ranges provided above, polymers having molecular weight ranges of at least 20,000 are preferred in some aspects for chemotherapeutic and organic moieties. In the case of some nucleophiles such as certain proteins, enzymes and the like, polymers having a molecular weight range of from about 2,000 to about 20,000 are preferred.

The polymeric substances includes herein are preferably water-soluble at room temperature. A non-limiting list of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained.

As an alternative to PAO-based polymers, effectively non-antigenic materials such as dextran, polyvinyl alcohols, carbohydrate-based polymers, hydroxypropylmethacrylamide (HPMA), and copolymers thereof, etc. and the like can be used if the same type of activation is employed as described herein for PAO's such as PEG. Those of ordinary skill in the art will realize that the foregoing list is merely illustrative and that all polymeric materials having the qualities described herein are contemplated. For purposes of the present invention, "effectively non-antigenic" means all polymeric materials understood in the art as being nontoxic and not eliciting an appreciable immune response in mammals.

F. Polymeric Double Prodrug Transport System Synthesis

Synthesis of representative, specific prodrugs is set forth in the Examples. Generally, however, the double prodrugs of the present invention can be prepared in several fashions. See FIG. 1. Thus, one method includes a. providing an intermediate compound (III)

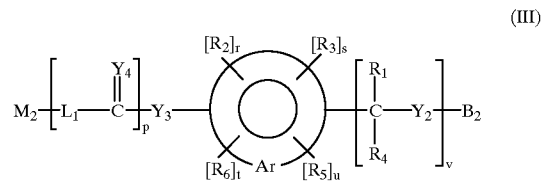

where M
2 is a cleavable or reversible protecting group, B$_2$ is H, OH,

or a leaving group and all other variable are as set forth above with regard to Formula (I).

b. removing the protecting group such as by treating the intermediate compound (IIIa) with a strong acid such as TFA (trifluoroacetic acid) or other trihaloacetic acid, HCl, sulfuric acid, etc., or tetrabutyl ammonium fluoride, c. reacting the resultant unprotected, intermediate compound (IIIa) with a moiety capable of reacting with a L$_t$ such a an activated polymer, i.e. a polymer having a reactive functional group, e.g. p-nitrophenyl or succinimidyl carbonate, carbonyl imidazole, thiazolidyl thione or the like, and optional spacer group, i.e. Cr$_9$R$_{10}$, to form an intermediate activated double prodrug transport form of formula (IV):

(IV)

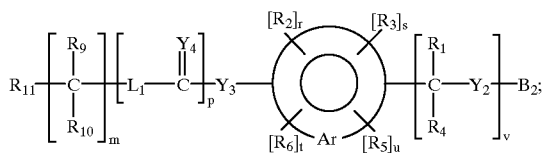

d. reacting the intermediate activated double prodrug transport form (IV) with an activating moiety donor such as p-nitrophenyl chloride (PNP-Cl) (forming, for example, compound (V) in FIG. 1); and optionally e. attaching an amine-containing or hydroxyl-containing compound residue, e.g. the drug to be transported, to compound (V) by displacig the leaving group in a substitution reaction with an amine- or hydroxyl-containing compound benzyl derivative. Similar techniques are employed when other aromatic moieties are used as starting materials.

Alternatively, as also shown in FIG. 1 with an amine-containing compound for illustrative purposes, the double prodrug can be prepared by a. providing an intermediate compound (III) as shown in the first method above and reacting it with an activating moiety donor such as p-nitrophenyl chloride (PNP—Cl) forming (VI) in FIG. 1;

b. attaching an amine-containing or hydroxyl-containing compound, e.g. the drug to be transported, to the activated intermediate compound (VI);

c. removing the protecting group to form VII in FIG. 1 (in the same manner as described above); and d. reacting the unprotected intermediate (VIII in FIG. 1) with an activated polymer to form the double prodrug.

Although not illustrated in FIG. 1, the reaction scheme for a hydroxyl-containing compound would nonetheless proceed in a similar manner.

As shown in FIG. 1, intermediate compound (III) can be prepared using standard organic synthesis techniques in which a hydroxy benzyl alcohol or other hydroxy aromatic alcohol is acylated with a spacer providing moiety.

In the third method illustrated in FIG. 1, a hydroxy or amino aromatic alcohol such as hydroxy-benzyl or amino-benzyl alcohol is reacted with an activated polymer to form (IV) which is then converted to the final product following steps d) and e) of the first method described above.

Examples of suitable o-hydroxybenzyl alcohols include 6-hydroxybenzyl alcohol, 6-hydroxy-3,5-dimethylbenzyl alcohol, 6-hydroxy-3,5-dimethoxybenzyl alcohol, 6-hydroxy-3-methoxybenzyl alcohol.

Examples of suitable p-hydroxybenzyl alcohols include 4-hydroxybenzyl alcohol, 4-hydroxy-3,5-dimethylbenzyl alcohol, 4-hydroxy-3,5-dimethoxybenzyl alcohol, 4-hydroxy-3-methoxybenzyl alcohol.

Examples of suitable aminobenzyl alcohols include 2-aminobenzyl alcohol, 4-aminobenzyl alcohol, and 2-amino-3-methyl-or 3-alkyl benzyl alcohols.

Preferably, the final prodrugs are prepared in an inert solvent such as methylene chloride, chloroform, toluene, DMF or mixtures thereof. The reaction also preferably is conducted in the presence of a base, such as dimethylaminopyridine, diisopropylethylamine, pyridine, triethylamine, etc). to neutralize any acids generated and at a temperature from −10° C. up to about 45° C. The resulting conjugated prodrug composition is then recovered or isolated using techniques known to those of ordinary skill, i.e. filtered, recrystallized.

The Leaving Group or Residue Portion "B"

1. Leaving Groups

In those aspects where leaving group, suitable leaving groups include, without limitations, moieties such as N-hydroxybenzotriazolyl, halogen, N-hydroxyphthalimidyl, p-nitrophenoxy, imidazolyl, N-hydroxysuccinimidyl, thiazolidinyl thione, or other good leaving groups as will be apparent to those of ordinary skill. The synthesis reactions used and described herein will be understood by those of ordinary skill without undue experimentation.

For example, the acylated intermediate compound (III) can be reacted with such as 4-nitrophenyl-chloroformate, disuccinimidyl carbonate (DSC), carbonyldiimidazole, thiazolidine thione, etc. to provide the desired activated derivative.

The acylation of the p-hydroxybenzyl alcohol or the p-aminobenzyl alcohol and the o-hydroxybenzyl alcohol or the o-aminobenzyl alcohol can be carried out with, for example, thiazolidine thione activated polymers, succinimidyl carbonate activated polymers, carboxylic acid activated polymers, blocked amino acid derivatives.

Once in place, the "activated" form of the PEG prodrug (or blocked prodrug) is ready for conjugation with an amine- or hydroxyl-containing compound. Some preferred activated transport forms are shown below.

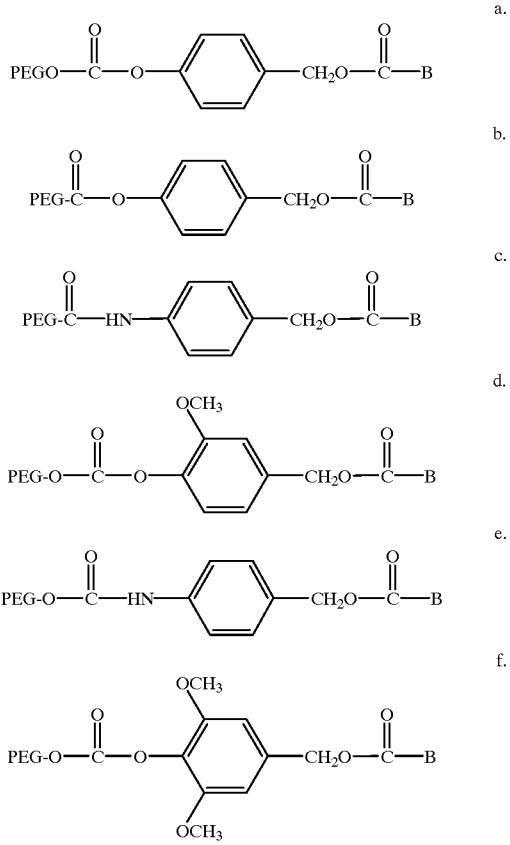

g.
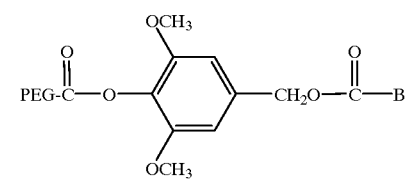
h.
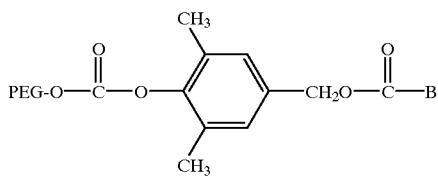
i.
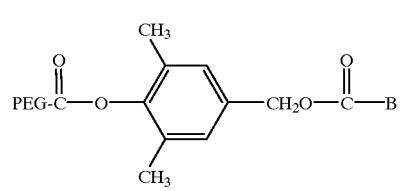
j.
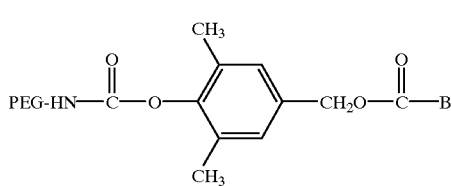
k.
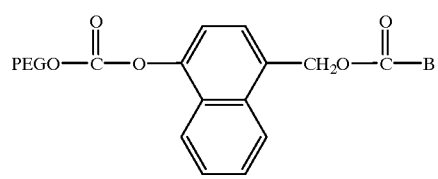
l.
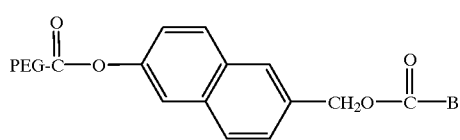
m.
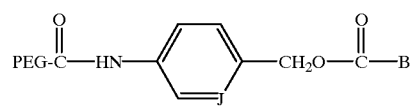
n.
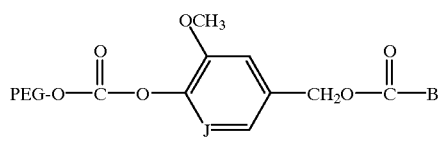
o.
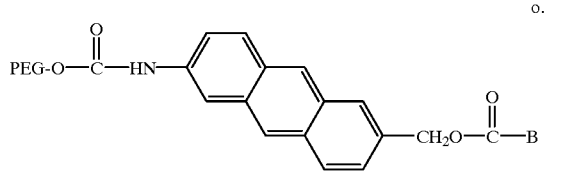
p.
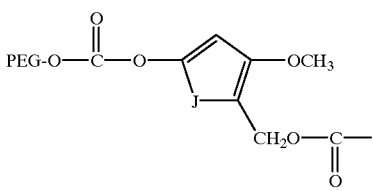
q.
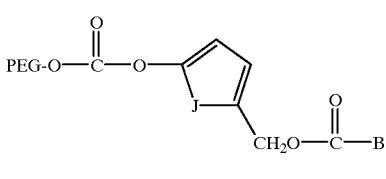
r.
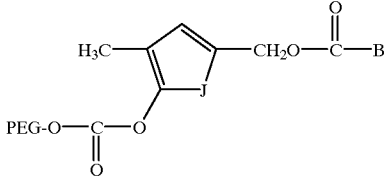
s.
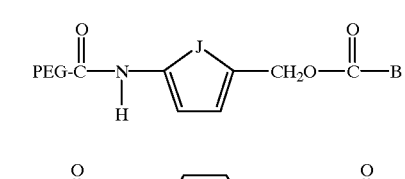
t.
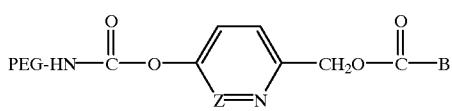
u.
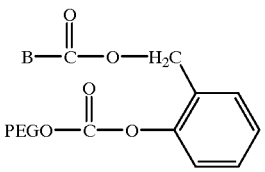
v.
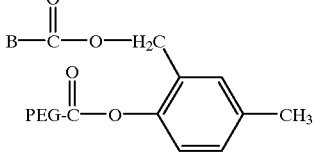
w.
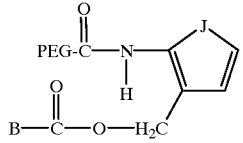
x.
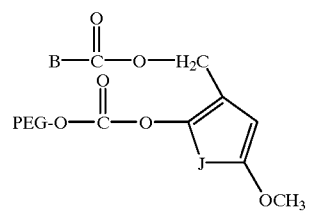

17

-continued

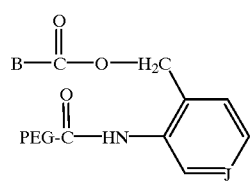

and

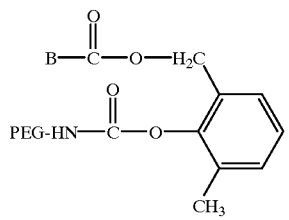

2. Residues of Amine-containing Compounds

In some aspects of the invention, e.g. after the prodrug transport has been formed, B is a residue of an amine-containing compound, a non-limiting list of such suitable compounds include residues of organic compounds, enzymes, proteins, polypeptides, etc. Organic compounds include, without limitation, moieties such as anthracycline compounds including daunorubicin, doxorubicin, p-aminoaniline mustard, melphalan, Ara-C (cytosine arabinoside) and related anti-metabolite compounds, e.g., gemcitabine, etc. Alternatively, B can be a residue of an amine-containing cardiovascular agent, anti-neoplastic, anti-infective, anti-fungal such as nystatin and amphotericin B, anti-anxiety agent, gastrointestinal agent, central nervous system-activated agent, analgesic, fertility agent, contraceptive agent, anti-inflammatory agent, steroidal agent, anti-urecemic agent, vasodilating agent, vasoconstricting agent, etc.

Suitable proteins, polypeptides, enzymes, peptides and the like having at least one available amino group for polymer attachment include materials which have physiological or pharmacological activities as well as those which are able to catalyze reactions in organic solvents. The only other requirement of the amine-containing materials is that they maintain at least some portion of the activity associated with the unmodified protein, enzyme, peptide, etc. after the prodrug transport portion has hydrolyzed.

Proteins, polypeptides and peptides of interest include, but are not limited to, hemoglobin, serum proteins such as blood factors including Factors VII, VIII, and IX, immunoglobulins, cytokines such as interleukins, i.e. IL-1 through IL-13, α-, β- and γ- and consensus interferons, colony stimulating factors including granulocyte colony stimulating factors, platelet derived growth factors and phospholipase-activating protein (PLAP). Other proteins of general biological or therapeutic interest include insulin, plant proteins, such as lectins and ricins, tumor necrosis factors and related proteins, growth factors such as transforming growth factors, such as TGFα's or TGFβ's and epidermal growth factors, hormones, somatomedins, erythropoietin, pigmentary hormones, hypothalmic releasing factors, antidiuretic hormones, prolactin, chorionic gonadotroptin, follicle-stimulating hormone, thyroid-stimulating hormone, tissue plasminogen activator, and the like. Immunoglobulins of interest include IgG, IgE, IgM, IgA, IgD and fragments thereof.

18

Some proteins as the interleukins, interferons and colony stimulating factors also exist in non-glycosylated form, usually as a result of using recombinant techniques. The non-glycosylated versions are also among the proteins of the present invention.

Enzymes of interest include carbohydrate-specific enzymes, proteolytic enzymes, oxidoreductases, transferases, hydrolases, lyases, isomerases and ligases. Without being limited to particular enzymes, examples of enzymes of interest include asparaginase, arginase, arginine deaminase, adenosine deaminase, superoxide dismutase, endotoxinases, catelases, chymotrypsin, lipases, uricases, adenosine diphosphatase, tyrosinases and bilirubin oxidase. Carbohydrate-specific enzyme of interest include glucose oxidases, glucodases, galactosidases, glucocerebrosidases, glucouronidases, etc.

Also included herein is any portion of a polypeptide demonistrating in vivo bioactivity. This includes amino acid sequences, nucleic acids (DNA, RNA) peptide nucleic acids (PNA), antibody fragments, single chain binding proteins, see, for example U.S. Pat. No. 4,946,778, disclosure of which is incorporated herein by reference, binding molecules including fusions of antibodies or fragments, polyclonal antibodies, monoclonal antibodies and catalytic antibodies.

The proteins or portions thereof can be prepared or isolated by using techniques known to those of ordinary skill in the art such as culture, extraction from animal sources, or by recombinant DNA methodologies. Transgenic sources of the proteins, polypeptides, amino acid sequences and the like are also contemplated. Such materials are obtained from transgenic animals, i.e., mice, pigs, cows, etc., wherein the proteins are expressed in milk, blood or tissues Transgenic insects and baculovirus expression systems are also contemplated as sources. Moreover, mutant versions of proteins, such as mutant interferons are also within the scope of the invention.

Other proteins of interest are allergen proteins such as ragweed, Antigen E, honeybee venom, mite allergen, and the like. The foregoing is illustrative of the proteins which are suitable for the present invention. It is to be understood that those proteins, as defined herein, not specifically mentioned but having an available amino group are also intended and are within the scope of the present invention.

In a preferred aspect of the invention, the amino-containing compound is a biologically active compound that is suitable for medicinal or diagnostic use in the treatment of animals, e.g., mammals, including humans, for condition for which such treatment is desired. The foregoing list is meant to be illustrative and not limiting for the compounds which can be modified. Those of ordinary skill will realize that other such compounds can be similarly modified without undue experimentation. It is to be understood that those biologically active materials not specifically mentioned but having suitable amino-groups are also intended and are within the scope of the present invention.

The only limitations on the types of amino-containing molecules suitable for inclusion herein is that there is available at least one (primary or secondary) amine containing position which can react and link with a carrier portion and that there is not substantial loss of bioactivity after the double prodrug system releases and regenerates the parent compound.

It is noted that parent compounds suitable for incorporation into the double prodrug compositions of the invention, may themselves be substances/compounds which are not active after hydrolytic release from the linked composition, but which will become active after undergoing a further chemical process/reaction. For example, an anticancer drug that is delivered to the bloodstream by the double prodrug transport system, may remain inactive until entering a cancer or tumor cell, whereupon it is activated by the cancer or tumor cell chemistry, e.g., by an enzymatic reaction unique to that cell.

After conjugation, the remaining amine-containing compound is referred to as the residue of the unconjugated compound 3. Residues of Hydroxyl-Containing Compounds a. Camptotecin and Related Topoisomerase I Inhibitors Camptothecin is a water-insoluble cytotoxic alkaloid produced by *Camptotheca accuminata* trees indigenous to China and *nothapodytes foetida* trees indigenous to India. Camptothecin and related compounds and analogs are also known to be potential anticancer or antitumor agents and have been shown to exhibit these activities in vitro and in vivo. Camptothecin and related compounds are also candidates for conversion to the double prodrugs of the present invention. Camptothecin and certain related analogues share the structure:

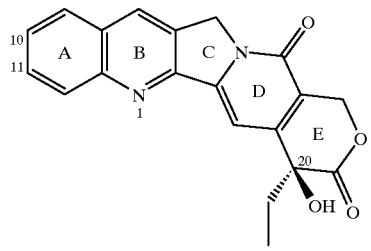

From this core structure, several known analogs have been prepared. For example, the A ring in either or both of the 10- and 11-positions can be substituted with an OH. The A ring can also be substituted in the 9-position with a straight or branched $C_{1+}$alkyl or $C_{3-1}$ alkoxy, optionally linked to the ring by heteroatom i.e. —O or S. The B ring can be substituted in the 7-position with a straight or branched $C_{1-30}$ alkyl or substituted alkyl-, $C_{5-8}$ cycloalkyl $C_{1-30}$ alkoxy, phenyl alkyl, etc., alkyl carbamate, alkyl carbazides, phenyl hydrazine derivatives, amino-, aminoalkyl-, aralkyl, etc. Other substitutions are possible in the C, D and E rings. See, for example, U.S. Pat. Nos. 5,004,758; 4,943,579; Re 32,518, the contents of which are incorporated herein by reference. Such derivatives can be made using known synthetic techniques without undue experimentation. Preferred camptothecin derivatives for use herein include those which include a 20-OH or another OH moiety which is capable of reacting directly with activated forms of the polymer transport systems described herein or to the linking moiety intermediates, e.g. iminodiacetic acid, etc., which are then attached to a polymer such as PEG. Reference to camptothecin analogs herein ha been made for purposes of illustration and not limitation.

b. Taxanes and Paclitaxel Derivatives

One class of compounds included in the double prodrug compositions of the present invention is taxanes. For purposes of the present invention, the term "taxane" includes all compounds within the taxane family of terpenes. Thus, taxol (paclitaxel), 3'-substituted tert-butoxy-carbonyl-amine derivatives (taxoteres) and the like as well as other analogs which are readily synthesized using standard organic techniques or are available from commercial sources such as Sigma Chemical of St. Louis, Mo. are within the scope of the present invention. Representative taxanes are shown below.

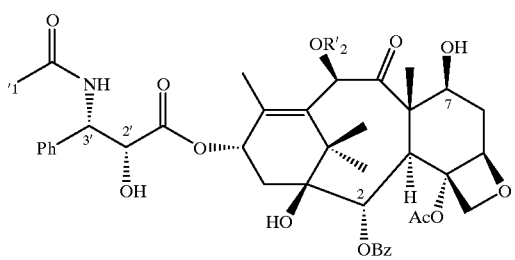

Paclitaxel: $R'_1 = C_6H_5$; $R'_2 = CH_3CO$;
Taxotere: $R'_1 = (CH_3)_3CO$; $R'_2 = H$ These derivatives have been found to be effective anticancer agents. Numerous studies indicate that the agents have activity against several malignancies. To date, their use has been severely limited by, among other things, their short supply, poor water solubility and hypersensitivity. It is to be understood that other taxanes including the 7-aryl-carbamates and 7-carbazates disclosed in commonly assigned U.S. Pat. Nos. 5,622,986 and 5,547,981 can also be included in the double prodrugs of the present invention. The contents of the foregoing U.S. patents are incorporated herein by reference. The only limitation on the taxane is that it must be capable of undergoing a hydroxyl based substitution reaction such as at the 2' position. Pacitaxel, however, is a preferred taxane.

c. Additional Biologically-Active Moieties

In addition to the foregoing molecules, the double prodrug formulations of the present invention can be prepared using many other compounds. For example, biologically-active compounds such as gemcitabine:

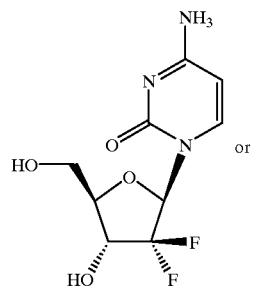

or etoposide:

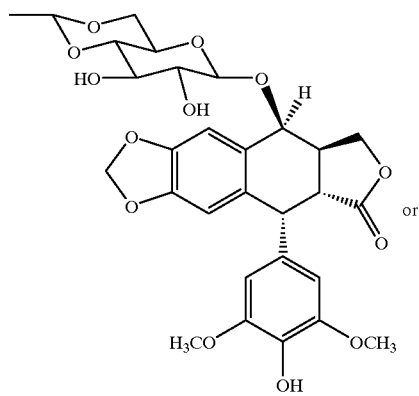

triazole-based antifungal agents such as fluconazole:

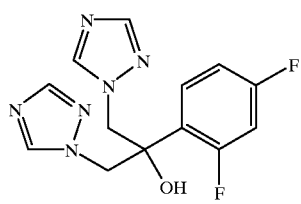

or ciclopirox:

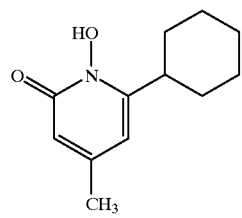

can be used.

The parent compounds selected for double prodrug forms need not be substantially water-insoluble, although the polymer-based double prodrugs of the present invention are especially well suited for delivering such water-insoluble compounds. Other useful parent compounds include, for example, certain low molecular weight biologically active proteins, enzymes and peptides, including peptido glycans, as well as other anti-tumor agents; cardiovascular agents such as forskolin; anti-neoplastics such as combretastatin, vinblastin, doxorubicin, Ara-C, maytansin, etc; anti-infectives such as vancomycin, erythromycin, etc.; anti-fungals such as nystatin, amphoteracin B, triazoles, papulocandins, pneumocandins, echinocandins, polyoxins, nikkomycins, pradimicins, benanomicins, etc. see, "Antibotics That Inhibit Fungal Cell Wall Development" *Annu. Rev. Microbiol.* 1994, 48:471–97, the contents of which are incorporated herein by reference, anti-anxiety agents, gastrointestinal agents, central nervous system-activating agents, analgesics, fertility or contraceptive agents, anti-inflammatory agents, steroidal agents, anti-urecemic agents, cardiovascular agents, vasodilating agents, vasoconstricting agents and the like.

It is noted that parent compounds suitable for incorporation into the double prodrug compositions of the invention, may themselves be substances/compounds which are not active after hydrolytic release from the linked composition, but which will become active after undergoing a further chemical process/reaction. For example, an anticancer drug that is delivered to the bloodstream by the double prodrug transport system, may remain inactive until entering a cancer or tumor cell, whereupon it is inactivated by the cancer or tumor cell chemistry, e.g., by an enzymatic reaction unique to that cell.

After conjugation, the remaining amine-or hydroxyl-containing compound is referred to as the residue of the unconjugated compound.

4. Polymeric Hybrids

In another aspect of the invention there are provided hybrid types of the polymeric double prodrug transport system described herein. In particular, the hybrid system includes not only the reversible double prodrug system described above but also a second polymeric transport system based on more permanent types of linkages. The hybrids can be prepared by at least two methods. For example, the benzyl-elimination-based double prodrug can be synthesized first and then PEGylated using any art-recognized activated polymer such as thiazolidinyl thione- or succinimidyl carbonate-activated PEG. Alternatively, the more permanent conjugation reaction can be performed first and the resultant conjugates can be used to for the double prodrug conjugates described herein. It will be understood that the hybrid systems will be better suited for proteins, enzymes and the like where multiple amino groups are available for attachment of the polymeric transport forms. For purposes of the present invention, "activated polymers" will be understood to include polymers containing one or more terminal groups which are capable of reacting with one or more of α-amino groups, ε-amino groups, histidine nitrogens, carboxyl groups, sulfhydryl groups, etc. found on enzymes, proteins etc., as well as such groups found on synthetically prepared organic compounds. It will further be appreciated that the activating groups described below can also be used to form the activated transport forms described above.

The activating terminal moiety can be any group which facilitates conjugation of the polymers with the biologically active material, i.e. protein, enzyme, etc. either before or after the double prodrug transport system of the present invention has been synthesized. See, for example, U.S. Pat. No. 4,179,337, the disclosure of which is hereby incorporated by reference. Such activating groups can be a moiety selected from:

I. Functional groups capable of reacting with an amino group such as
  a) carbonates such as the p-nitrophenyl, or succinimidyl; see, for example, U.S. Pat. No. 5,122,614, the disclosure of which is hereby incorporated by reference;
  b) carbonyl imidazole;
  c) azlactones; see, for example, U.S. Pat. No. 5,349,001, the disclosure of which is hereby incorporated by reference;
  d) cyclic imide thiones see, for example, U.S. Pat. No. 5,349,001, the disclosure of which is hereby incorporated by reference;
  e) isocyanates or isothiocyanates; or
  f) active esters such as N-hydroxy-succinimidyl or N-hydroxybenzotriazolyl.

II. Functional groups capable of reaction with carboxylic acid groups and reactive carbonyl groups such as:
  a) primary amines; or
  b) hydrazine and hydrazide functional groups such as the acyl hydrazides, carbazates, semicarbamates, thiocarbazates, etc.

III. Functional groups capable of reacting with mercapto or sulfhydryl groups such as phenyl glyoxals; see, for example, U.S. Pat. No. 5,093,531, the disclosure of which is hereby incorporated by reference;

IV. Functional groups capable of reacting with hydroxyl groups such as (carboxylic) acids or other nucleophiles capable of reacting with an electrophilic center. A non-limiting list includes, for example, hydroxyl, amino, carboxyl, thiol groups, active methylene and the like.

The activating moiety can also include a spacer moiety located proximal to the polymer. The spacer moiety may be a heteroalkyl, alkoxy, alkyl containing up to 18 carbon atoms or even an additional polymer chain. The spacer moieties can added using standard synthesis techniques.

Methods of Treatment

Another aspect of the present invention provides methods of treatment for various medical conditions in mammals. The methods include administering to the mammal in need of such treatment, an effective amount of a composition of the invention, as described herein, such as a double prodrug of doxorubicin. The prodrug compositions are useful for, among other things, treating diseases which are similar to those which are treated with the parent compound, e.g. enzyme replacement therapy, neoplastic disease, reducing tumor burden, preventing metastasis of neoplasms and preventing recurrences of tumor/neoplastic growths in mammals.

The amount of the prodrug that is administered will depend upon the amount of the parent molecule included therin. Generally, the amount of prodrug used in the treatment methods is that amount which effectively achieves the desired therapeutic result in mammals. Naturally, the dosages of the various prodrug compounds will vary somewhat depending upon the parent compound, rate of in vivo hydrolysis, molecular weight of the polymer, etc. In general, double prodrug polymeric derivatives are administered in amounts ranging from about 5 to about 500 mg/m$^2$ per day, based on the native drug. The range set forth above is illustrative and those skilled in the art will determine the optimal dosing of the prodrug selected based on clinical experience and the treatment indication. Actual dosages will be apparent to the artisan without undue experimentation.

The compositions, including prodrugs, of the present invention can be included in one or more suitable pharmaceutical compositions for administration to mammals. The pharmaceutical compositions may be in the form of a solution, suspension, tablet, capsule or the like, prepared according to methods well known in the art. It is also contemplated that administration of such compositions may be by the oral and/or parenteral routes depending upon the needs of the artisan. A solution and/or suspension of the composition may be utilized, for example, as a carrier vehicle for injection or infiltration of the composition by any art known methods, e.g., by intravenous, intramuscular, subdermal injection and the like.

Such administration may also be by infusion into a body space or cavity, as well as by inhalation and/or intranasal routes. In preferred aspects of the invention, however, the prodrugs are parenterally administered to mammals in need thereof.

EXAMPLES

The following examples serve to provide further appreciation of the invention but are not meant in any way to restrict the effective scope of the invention. The compound numbers mentioned in the examples refer to the compounds identified in FIGS. 2–6.

Example 1

Synthesis of compound (2a):

A solution of 10.0 g (2.0 mmol) of mPEG 5 kDa thiazolidine thione activated carbamate, 0.5 g (4.0 mmol) of 4-hydroxybenzyl alcohol and 0.5 g (4.0 mmol) of 4-(dimethylamino)pyridine (DMAP) in 50 mL of dry methylene chloride was refluxed for 18 hours. The solvent was removed from the reaction mixture by distillation in vacuo followed by crystallization of the residue from 2-propanol to yield 9.0 g (87% yield) of alcohol 1a.

$^{13}$C NMR (67.80 MHz, CDCl$_3$) δ 58.15, 62.97, 66.86–71.14 (PEG), 120.01, 126.98, 138.97, 149.35, 152.79.

A solution of 5.0 g (1.0 mmol) of 1a in 75 mL of toluene was azeotroped for 2 hours while removing 25 ml of toluene/water. The reaction mixture was cooled to 30° C. followed by the addition of 0.4 g (2.0 mmol) of 4-nitrophenylchloroformate (PNP-Cl) and 0.26 g (2.0 mmol) of diisopropylethylamine (DIEA). This mixture was stirred for 18 hours at 50–55° C. followed by cooling and removal of the solvent by distillation in vacuo. The residue was crystallized from 20% methylene chloride in ethyl ether to yield 3.7 g (70% yield) of product 2a.

$^{13}$C NMR (67.80 MHz CDCl$_3$) δ 58.25, 67.14–71.21 (PEG), 120.72, 121.24, 124.58, 129.32, 131.44, 144.71, 150.79, 154.78, 151.63, 152.64.

Example 2

Synthesis of compound (2b):

Compound 2b is prepared in a similar manner to compound 2a using a 40 kDa PEG dithiazolidine thione carbamate in place of the 5 kDa PEG.

Example 3

Synthesis of compound (4a):

A solution of 10.0 g (2.0 mmol) of mPEG 5 kDa acid, 1.0 g (8.0 mmol) of 4-hydroxybenzyl alcohol and 1.0 g (8.0 mmol) of DMAP in 100 mL of dry methylene chloride was cooled to 0° C. followed by the addition of 1.0 g (8.0 mmol) of diisopropylcarbodiimide (DIPC). The reaction mixture was allowed to slowly warm to room temperature overnight. The solvent was removed by distillation in vacuo, and the residue was crystallized from 2-propanol to yield 8.6 g (83% yield) of product 3a.

$^{13}$C NMR (67.80 MHz CDCl$_3$) δ 57.88, 62.65, 67.54–71.13 (PEG), 120.17, 126.77, 138.85, 148.20, 167.92.

Compound 3a can also be made using mPEG 5 kDa thiazolidine thione amide in place of the mPEG 5 kDa acid, in the presence of DMAP and 4-hydroxybenzyl alcohol in methylene chloride.

A solution of 3.0 g (0.58 mmol) of 3a in 75 mL of toluene was azeotroped for 2 hours while removing 25 mL of toluene/water. The reaction mixture was cooled to 30° C. followed by the addition of 0.23 g (1.1 mmol) of PNP-Cl and 0.15 g (1.2 mmol) of DIEA. This mixture was stirred for 18 hours at 50–55° C. followed by cooling and removal of the solvent by distillation in vacuo. The residue was crystallized from 20% methylene chloride in ethyl ether to yield 2.4 g (77% yield) of product 4a.

$^{13}$C NMR (67.80 MHz, CDCl$_3$) δ 57.90, 67.53–70.92 (PEG), 120.85, 121.06, 124.32, 129.03, 131.23, 144.42, 149.67, 154.52, 151.34, 167.79.

Example 4

Synthesis of compound (4b):

A solution of 4.0 g (0.1 mmol) of 40 kDa PEG-dithiazolidine thione amide, 0.26 g (2.1 mmol) of 4-hydroxybenzyl alcohol and 0.25 g (2.1 mmol) of DMAP in 40 mL of dry methylene chloride was refluxed overnight. The solvent was removed by distillation in vacuo, and the residue was crystallized from 2-propanol to yield 3.4 g (85% yield) of product 3b.

$^{13}$C NMR (67.80 MHz, CDCl$_3$) δ 63.57, 68.36–71.86 (PEG), 120.69, 127.31, 139.15, 149.25, 168.21.

A solution of 3.0 g (0.07 mmol) of 3b in 140 mL of toluene was azeotroped for 2 hours while removing 40 mL of toluene/water. The reaction mixture was cooled to 30° C. followed by the addition of 0.06 g (0.3 mmol) of PNP-Cl and 0.04 g (0.3 mmol) of DIEA. This mixture was stirred for 18 hours at 50–55° C. followed by cooling and removal of the solvent by distillation in vacuo. The residue was crystallized from 20% methylene chloride in ethyl ether to yield 2.4 g (77% yield) of product 4b.

$^{13}$C NMR (67.80 MHz, CDCl$_3$) δ 68.47–71.32 (PEG) 121.39, 121.47, 124.87, 129.45, 131.96, 145.54, 150.15, 155.01, 151.82, 168.19.

Example 5

Synthesis of compound (6a):

A solution of 2.5 g (0.5 mmol) of mPEG 5 kDa thiazolidine thione carbamate, 0.16 g (1.0 mmol) of 4-hydroxy-3,5-dimethylbenzyl alcohol and 0.12 g (1.0 mmol) of DMAP in 50 mL of dry methylene chloride was refluxed for 18 hours. The solvent was removed from the reaction mixture by distillation in vacuo followed by crystallization of the residue from 2-propanol to yield 2.2 g (85% yield) of alcohol 5a.

$^{13}$C NMR (67.80 MHz CDCl$_3$) δ 15.10, 57.94, 63.25, 66.96–71.71 (PEG), 126.30, 129.19, 138.87, 149.90, 152.12.

A solution of 2.2 g (0.42 mmol) of 5a in 75 mL of toluene was azeotroped for 2 hours while removing 25 mL of toluene/water. The reaction mixture was cooled to 30° C. followed by the addition of 0.17 g (0.85 mmol) of PNP-Cl and 0.11 g (0.85 mmol) of DIEA. This mixture was stirred for 18 hours at 50–55° C. followed by cooling and removal of the solvent by distillation in vacuo. The residue was crystallized from 20% methylene chloride in ethyl ether to yield 1.9 g (86%) of product 6a.

$^{13}$C NMR (67.80 MHz, CDCl$_3$) δ 15.28, 58.14, 67.32–71.50 (PEG), 121.19, 124.58, 128.31, 130.31, 131.65, 145.16, 148.39, 151.73, 152.09, 155.15

Example 6

Synthesis of compound (6b):

Compound 6b was prepared in a similar manner to compound 6a using a 40 kDa PEG dithiazolidine thione amide in place of the 5 kDa PEG.

$^{13}$C NMR (67.80 MHz, CDCl$_3$) δ 15.78, 63.86, 68.10, 68.71–71.58 (PEG), 126.71, 129.58, 139.87, 148.39, 152.09, 167.66.

Example 7

Synthesis of compound (6c):

A solution of 6.0 g (0.15 mmol) of (di-SC)-PEG 40 kDa and 0.6 g (4.0 mmol) of 3,5-dimethyl-4-hydroxy benzyl alcohol in 60 mL of dry methylene chloride was refluxed overnight. The solvent was removed by distillation in vacuo, and the residue was crystallized from 2-propanol to yield 5.4 g (90% yield of product 5c.

$^{13}$C NMR (67.80 MHz, CDCl$_3$) δ 15.49, 63.44, 67.06, 68.31, 68.58–70.90 (PEG), 126.53, 129.37, 138.79, 146.78, 152.36.

A solution of 2.0 g (0.05 mmol) of 5c in 80 mL of toluene was azetroped for 2 hours while removing 40 mL of toluene/water. The reaction mixture was cooled to 30° C. followed by the addition of 0.04 g (0.2 mmol) of PNP-Cl and 0.03 g (0.2 mmol) of DIEA. This mixture was stirred for 18 hours at 50–55° C. followed by cooling and removal of the solvent by distillation in vacuo. The residue was crystallized from 20% methylene chloride in ethyl ether to yield 1.7 g (85% yield) of product 6c.

$^{13}$C NMR (67.80 MHz, CDCl$_3$) δ 15.44, 67.21, 68.23, 68.61–71.26 (PEG), 121.29, 124.65, 128.54, 130.19, 131.41, 144.79, 148.11, 151.73, 152.14, 154.91.

Example 8

Synthesis of compound (8a):

A solution of 3.0 g (0.6 mmol) of mPEG 5 kDa thiazolidine thione activated carbamate, 0.24 g (1.3 mmol) of 4-hydroxy-3,5-dimethoxybenzyl alcohol and 0.16 g (1.3 mmol) of DMAP in 50 mL of dry methylene chloride was refluxed for 18 hours. The solvent was removed from the reaction mixture by distillation in vacuo followed by crystallization of the residue from 2-propanol to yield 2.8 g (90% yield) of alcohol 7a.

$^{13}$C NMR (67.80 MHz, CDCl$_3$) δ 55.64, 57.94, 63.69, 67.09–71.32 (PEG), 103.26, 129.15, 139.97, 151.70, 152.14.

A solution of 2.5 g (0.5 mmol) of 7a in 75 mL of toluene was azeotroped for 2 hours while removing 25 mL of toluene/water. The reaction mixture was cooled to 30° C. followed by the addition of 0.19 g (1.0 mmol) of PNP-Cl and 0.12 g (1.0 mmol) of DIEA. This mixture was stirred for 18 hours at 50–55° C. followed by cooling and removal of the solvent by distillation in vacuo. The residue was crystallized from 20% methylene chloride in ethyl ether to yield 2.3 g (88% yield) of 8a.

$^{13}$C NMR (67.80 MHz, CDCl$_3$) δ 56.08, 58.32, 67.59–71.63 (PEG), 105.51, 121.29, 124.76, 130.00, 132.53, 145.32, 151.88, 155.22, 152.09, 152.34, 152.35.

Example 9

Synthesis of compound (8b):

Compound 7b was prepared in a similar manner to compound 7a using a 40 kDa PEG dithiazolidine thione amide in place of the 5 kDa PEG.

$^{13}$C NMR (67.80 MHz, CDCl$_3$) δ 55.93, 64.27, 67.97, 68.68–72.04 (PEG), 103.60, 140.09, 152.01, 167.61.

Compound 8b was prepared in a similar manner to compound 8a using 7b in place of 7a.

$^{13}$C NMR (67.80 MHz, CDCl$_3$) δ 56.11, 67.98, 68.36–71.47, 105.56, 105.62, 124.79, 132.56, 145.46, 151.93, 152.38, 155.32, 167.46, 167.49.

Example 10

Synthesis of compound (10a):

A solution of 3.0 g (0.6 mmol) of mPEG 5 kDa thiazolidine thione carbamate, 0.2 g (1.3 mmol) of 4-hydroxy-3-methoxybenzyl alcohol and 0.14 g (1.1 mmol) of DMAP in 40 mL of dry methylene chloride was refluxed for 18 hours. The solvent was removed from the reaction mixture by distillation in vacuo followed by crystallization of the residue from 2-propanol to yield 2.4 g (77% yield) of product 9a.

$^{13}$C NMR (67.80 MHz, CDCl$_3$) δ 54.94, 57.94, 62.99, 66.82–70.97 (PEG), 110.13, 117.54, 120.95, 138.03, 140.38, 150.13, 152.25.

A solution of 2.2 g (0.42 mmol) of 9a in 70 mL of toluene was azeotroped for 2 hours while removing 30 mL of toluene/water. The reaction mixture was cooled to 30° C. followed by the addition of 0.20 g (0.9 mmol) of PNP-Cl and 0.11 g (0.9 mmol) of DIEA. This mixture was stirred for 18 hours at 50–55° C. followed by cooling and removal of the solvent by distillation in vacuo. The residue was crystallized from 20% methylene chloride in ethyl ether to yield 1.1 g (48% yield) of product 10a.

$^{13}$C NMR (67.80 MHz, CDCl$_3$) δ 55.84, 58.32, 67.54–71.62 (PEG), 112.97, 120.52, 121.29, 122.21, 124.75, 133.05, 140.64, 145.29, 151.21 and 155.22, 151.88, 152.51.

Example 11

Synthesis of compound (10b):

Compound 10b is prepared in a similar manner to compound 10a using a 40 kDa PEG dithiazolidine thione amide in place of the 5 kDa PEG.

Example 12

Synthesis of compound (12b):

A solution of 4.0 g (0.1 mmol) of disuccinimidyl (di-SC)-PEG 40 kDa, 0.1 g (0.8 mmol) of 4-aminobenzyl alcohol, and 0.1 g (0.8 mmol) of DMAP in 30 mL of dry methylene chloride was stirred overnight at room temperature. The solvent was removed by distillation in vacuo, and the residue crystallized from 2-propanol to yield 3.7 g (93% yield) of product 11b.

$^{13}$C NMR (67.80 MHz, CDCl$_3$) δ 63.64, 63.99, 68.91–71.32 (PEG), 118.57, 127.06, 136.13, 137.20, 153.08.

A solution of 3.0 g (0.07 mmol) of 11b in 140 mL of toluene was azeotroped for 2 hours while removing 40 mL of toluene/water. The reaction mixture was cooled to 30° C. followed by the addition of 0.06 g (0.3 mmol) of PNP-Cl and 0.04 g (0.3 mmol) of DIEA. This mixture was stirred for 18 hours at 50–55° C. followed by cooling and removal of the solvent by distillation in vacuo. The residue was crystallized from 20% methylene chloride in ethyl ether to yield 2.4 g (77% yield) of product 12b.

$^{13}$C NMR (67.80 MHz, CDCl$_3$) δ 64.01, 68.60–71.45 (PEG), 118.78, 121.39, 124.86, 127.29, 128.85, 129.19, 139.13, 155.51, 152.09, 153.19.

Example 13

Synthesis of compound (12a):

Compound 12a is prepared in a similar manner to 12b by using mPEG 5 kDa SC-PEG in place of the 40 kDa SC-PEG.

Example 14

Synthesis of compound (14a):

A solution of 5.0 g (1.0 mmol) of mPEG 5 kDa carboxylic acid, 0.6 g (5.0 mmol) of 4-aminobenzyl alcohol, 2.0 mL (3.0 mmol) of a 50% solution of 1-propanephosphonic acid cyclic anhydride (PPACA) in ethyl acetate and 0.4 g (3.0 mmol) of DMAP in 30 mL of dry methylene chloride was stirred for 18 hours at room temperature. The solvent was removed by distillation in vacuo, and the residue was crystallized from 2-propanol to yield 8.6 g (83% yield) of product 13a.

$^{13}$C NMR (67.80 MHz, CDCl$_3$) δ 58.07, 63.23, 69.31–71.06 (PEG), 118.97, 126.51, 135.82, 136.96, 167.28.

A solution of 3.0 g (0.58 mmol) of 13a in 75 mL of toluene was azetroped for 2 hours while removing 25 mL of toluene/water. The reaction mixture was cooled to 30° C. followed by the addition of 0.23 g (1.1 mmol) of PNP-Cl and 0.15 g (1.2 mmol) of DIEA. This mixture was stirred for 18 hours at 50–55° C. followed by cooling and removal of the solvent by distillation in vacuo. The residue was crystallized from 20% methylene chloride in ethyl ether to yield 2.6 g (84% yield) of product 14a.

$^{13}$C NMR (67.80 MHz, CDCl$_3$) δ 58.45, 69.57–71.4 (PEG), 119.61, 121.37, 124.75, 129.11, 129.42, 137.88, 144.86, 155.04, 151.86, 167.95.

Example 15

Synthesis of compound (14b):

A solution of 5.0 g (0.12 mmol) of PEG 40 kDa dicarboxylic acid, 0.15 g (1.2 mmol) of 4-aminobenzyl alcohol, 0.5 mL (0.8 mmol) of a 50% solution of PPACA in ethyl acetate and 0.09 g (0.8 mmol) of DMAP in 100 mL of dry methylene chloride was stirred overnight at room temperature. The solvent was removed by distillation in vacuo, and the residue was crystallized from 2-propanol to yield 2.54 g (56% yield) of product 13b.

$^{13}$C NMR (67.80 MHz, CDCl$_3$) δ 63.98, 68.99–71.0 (PEG), 119.60, 127.01, 136.50, 137.35, 167.48.

A solution of 3.0 g (0.07 mmol) of 13b in 140 mL of toluene was azeotroped for 2 hours while removing 40 mL of toluene/water. The reaction mixture was cooled to 30° C. followed by the addition of 0.06 g (0.3 mmol) of PNP-Cl and 0.04 g (0.3 mmol) of DIEA. This mixture was stirred for 18 hours at 50–55° C. followed by cooling and removal of the solvent by distillation in vacuo. The residue was crystallized from 20% methylene chloride in ethyl ether to yield 2.6 g (84% yield) of product 14b.

$^{13}$C NMR (67.80 MHz, CDCl$_3$) δ 69.00–71.97 (PEG), 119.78, 121.31, 124.75, 128.98, 129.84, 138.17, 144.86, 155.38, 151.67, 167.77.

Example 16

Synthesis of (18b):

A solution of t-Boc-aminoisobutyric acid (2.0 g, 10 mmol), 2.6 g (21.0 mmol) of 4-hydroxybenzyl alcohol, 4.0 g (21.0 mmol) of 1-ethyl-3-(3-dimethylaminopropyl)-carbodiimide hydrochloride (EDC), and 2.6 g (21.3 mmol) of DMAP in 100 mL of dry methylene chloride was stirred at room temperature overnight. The solvent was removed by distillation in vacuo, and the residue was crystallized from methanol to yield 2.6 g (83% yield) of product 15.

$^1$H NMR (270.05 MHz, CDCl$_3$) δ 1.45 (s, 9 H), 1.61 (s, 6 H), 4.64 (s, 2 H), 7.06 (d, 2 H, J=8.1 Hz), 7.35 (d, 2 H, J=8.1 Hz).

$^{13}$C NMR (67.80 MHz, CDCl$_3$) δ 25.38, 28.30, 56.13, 64.54, 121.39, 127.94, 138.55, 150.37, 154.68, 173.49.

Trifluoroacetic acid (TFA, 2.5 mL) was added to a solution of 1 g (3.2 mmol) of 15 in 5 mL of methylene chloride followed by stirring at room temperature for 30 minutes. Ether was added until the solid precipitated. The solid was filtered and washed thoroughly with ether until all the excess TFA is removed. The TFA salt 16 was dried and used as such in the next step.

A solution of 2.0 g (0.05 mmol) of 40 kDa PEG dithiazolidine thione amide, 0.065 g (0.2 mmol) of 16, and 0.05 g (0.4 mmol) of DMAP in 30 mL of dry methylene chloride was refluxed for 18 hours. The solvent was removed by distillation in vacuo, and the residue was recrystallized from 2-propanol to yield 1.9 g (95% yield) of product 17b.

$^{13}$C NMR (67.80 MHz, CDCl$_3$) δ 24.49, 55.24, 63.49, 68.65–71.26 (PEG), 120.85, 127.21, 138.79, 168.99.

Compound 18b was prepared in a similar manner as 14b by using 17b in the place of 13b.

Example 17

Synthesis of compound (18a):

Compound 18a is prepared in a similar manner as 18b by using 5 kDa PEG thiazolidine thione amide in the place of 40 kDa PEG.

Example 18

Synthesis of compound (21a):

A solution of 10.0 g (2.0 mmol) of mPEG 5 kDa isocyanate, 0.5 g (4.0 mmol) of 4-hydroxybenzaldehyde and 0.5 g (4.0 mmol) of DMAP in 50 mL of dry methylene chloride was refluxed for 18 hours. The solvent was removed from the reaction mixture by distillation in vacuo followed by crystallization of the residue from 2-propanol to yield the aldehyde 19a.

To a solution of 0.25 g (0.05 mmol) of this aldehyde in 40 mL of methanol at 0° C. was added 6.0 mg (0.15 mmol) of sodium borohydride followed by stirring for 2 hours. The solvent was removed from the reaction mixture by distillation in vacuo followed by dissolving the residue in 30 mL of methylene chloride and washing with dilute aqueous HCl. The organic layer was separated and dried over anhydrous sodium sulfate. The solvent was removed by distillation in vacuo, and the residue was crystallized from 2-propanol to yield 1.5 g (75% yield) of 20b.

A solution of 5.0 g (1.0 mmol) of 20a in 75 mL of toluene was azeotroped for 2 hours while removing 25 mL of toluene/water. The reaction mixture was cooled to 30° C. followed by the addition of 0.4 g (2.0 mmol) of PNP-Cl and 0.26 g (2.0 mmol) of DIEA. This mixture was stirred for 18 hours at 50–55° C. followed by cooling and removal of the solvent by distillation in vacuo. The residue was crystallized from 20% methylene chloride in ethyl ether to yield 3.7 g (70% yield) of product 21a.

$^{13}$C NMR (67.80 MHz, CDCl$_3$) δ 40.66, 58.58, 68.92–71.54 (PEG), 121.45, 121.57, 124.86, 129.17, 129.51, 130.66, 145.00, 151.32, 151.96, 154.03, 155.12.

Example 19

Synthesis of (21b):

Compound 20b was prepared in a similar manner as 20a by using 40 kDa PEG kDa diisocyanate in place of 5 k mPEG isocyanate.

$^{13}$C NMR (67.80 MHz, CDCl$_3$) δ 40.35, 63.44, 67.97–71.45 (PEG), 120.82, 127.05, 137.99, 147.68, 154.13.

Compound 21b was prepared in a similar manner as 21a using 20b in the place of 20a.

$^{13}$C NMR (67.80 MHz, CDCl$_3$) δ 40.72, 67.81–71.99 (PEG), 121.53, 121.66, 121.96, 124.68, 124.96, 125.20, 129.63, 130.73, 145.07, 151.37, 152.05, 154.12, 155.81.

Example 20

Synthesis of compound (22a):

A mixture of 0.5 g (0.09 mmol) of 2a, 65 mg (0.11 mmol) of doxorubicin hydrochloride and 46 mg (0.38 mmol) of DMAP in 10 mL of dry dimethylformamide was stirred at room temperature for 18 hours. To this mixture was added 30 mL of ether. The precipitate was collected by filtration and washed with ether followed by crystallization from 2-propanol to yield 0.38 g (70% yield) of product 22a.

$^{13}$C NMR (67.80 MHz, CDCl$_3$) δ 16.38, 29.25, 33.13, 34.93, 42.11, 44.71, 46.58, 56.01, 58.32, 64.76, 64.93, 67.06, 68.06, 68.26, 68.81, 68.99–71.26 (PEG), 75.91, 100.32, 110.54, 110.68, 118.06, 119.04, 119.98, 120.37, 120.66, 128.65, 129.16, 132.98, 133.27, 133.91, 134.60, 135.19, 150.09, 152.75, 154.86, 155.56, 160.34, 185.80, 186.10, 213.07.

Example 21

Synethesis of (23a)

A mixture of 0.5 g (0.09 mmol) of 2a, 65 mg (0.11 mmol) of daunorubicin hydrochloride and 46 mg (0.38 mmol) of DMAP in 10 mL of dry dimethylformamide was stirred at room temperature for 18 hours. To this mixture was added 30 mL of ether. The precipitate was collected by filtration and washed with ether followed by crystallization from 2-propanol to yield 0.44 g (80% yield) of product.

$^{13}$C NMR (67.80 MHz, CDCl$_3$) δ 16.52, 24.47, 29.69, 32.87, 34.62, 44.97, 46.88, 56.29, 58.58, 65.23, 67.03, 67.30, 68.31, 68.26, 68.68, 69.39–71.50 (PEG), 76.25, 100.73, 110.73, 110.68, 110.91, 118.16, 119.31, 120.40, 120.59, 120.90, 128.85, 129.38, 133.88, 134.09, 135.01, 135.35, 153.03, 155.10, 155.38, 156.03, 160.60, 186.16, 186.47, 211.77.

Example 22

A mixture of 0.5 g (0.09 mmol) of 4a, 65 mg (0.11 mmol) of daunorubicin hydrochloride and 46 mg (0.38 mmol) of DMAP in 10 mL of dry dimethylformamide was stirred at room temperature for 18 hours. To this mixture was added 30 mL of ether. The precipitate was collected by filtration and washed with ether followed by crystallization from 2-propanol to yield 0.38 g (75% yield) of product 24a.

$^{13}$C NMR (67.80 MHz, CDCl$_3$) δ 16.25, 24.07, 29.10, 32.35, 34.27, 46.62, 55.93, 58.22, 64.87, 66.75, 67.81, 68.24, 68.50, 68.60, 68.83–71.19 (PEG), 75.90, 100.19, 110.34, 110.51, 117.97, 118.91, 119.91, 120.66, 120.87, 128.60, 129.38, 133.66, 133.86, 134.54, 135.06, 154.81, 154.93, 155.62, 156.03, 160.26, 168.08, 185.71, 185.95, 211.17.

Example 23

Synthesis of (24b)

Compound 24b was prepared in a similar manner to compound 24a using a 40 kDa MW PEG linker 4b in place of MW 5 kDa linker 4a. UV assay for this compound indicated the amount of daunorubicin present is 2.3%. In vitro and in vivo results for this compound are set forth in Table 1 below.

Example 24

A mixture of 0.5 g (0.09 mmol) of 10a, 65 mg (0.11 mmol) of daunorubicin hydrochloride and 46 mg (0.38 mmol) of DMAP in 10 mL of dry dimethylformamide was stirred at room temperature for 18 hours. To this mixture was added 30 mL of ether. The precipitate was collected by filtration and washed with ether followed by crystallization from 2-propanol to yield 0.44 g (80% yield) of product. UV assay for this compound indicated the amount of daunorubicin present is 9.2%.

Example 25

Synthesis of (26a)

A mixture of 0.5 g (0.09 mmol) of 8a, 65 mg (0.11 mmol) of daunorubicin hydrochloride and 46 mg (0.38 mmol) of DMAP in 10 mL of dry dimethylformamide was stirred at room temperature for 18 hours. To this mixture was added 30 mL of ether. The precipitate was collected by filtration and washed with ether followed by crystallization from 2-propanol to yield 0.42 g (81% yield) of product. UV assay for this compound indicated the amount of daunorubicin present is 9.2%.

Example 26

Synthesis of compound (26b)

Compound 26b was prepared in a similar manner to compound 26a using a 40 kDa PEG linker 8b in place of 5 kDaPEG linker 8a. UV assay for this compound indicated the amount of daunorubicin present is 2.1%.

Example 27

Synthesis of (27a)

A mixture of 0.5 g (0.09 mmol) of 6a, 65 mg (0.11 mmol) of daunorubicin hydrochloride and 46 mg (0.38 mmol) of DMAP in 10 mL of dry dimethylformamide was stirred at room temperature for 18 hours. To this mixture was added 30 mL of ether. The precipitate was collected by filtration and washed with ether followed by crystallization from 2-propanol to yield 0.44 g (85% yield) of product. UV assay for this compound indicated the amount of daunorubicin present is 9.2%.

Example 28

Synthesis of compound (27b)

Compound 27b was prepared in a similar manner to compound 27a using a 40 kDa PEG linker 6b in place of 5 kDaPEG linker 6a. UV assay for this compound indicated the amount of daunorubicin present is 2.3%. In vitro and in vivo results for this compound are set forth in Table 1 below.

Example 29

Synthesis of compound (27c)

Compound 27c was prepared in a similar manner to compound 27a using a 40 kDa PEG linker 6c in place of 5 kDaPEG linker 6a. UV assay for this compound indicated the amount of daunorubicin present is 2.5%.

Example 30

Synthesis of compound (27d)

A mixture of 1.5 g (0.037 mmol) of 6c, 50 mg (0.19 mmol) of p-amino-(N,N-di-2-chloroethyl)aniline hydrochloride (synthesized using a modified procedure of Edwards et al. Cytotoxic Compounds. Part XVII. o-, m-, and p-(Bis-2-chloroethylamino)phenol, p-[N-(2-Chloethyl)methylamino]phenol, N,N-Bis-2-chloroethyl-p-phenylenediamine, and N,N-Bis-2-chloroethyl-N'-methyl-p-phenylenediamine as Sources of Biologically Active Carbamates. JCS Perkin I, 1973, 2397), and 50 mg (0.41 mmol) of DMAP in 15 mL of anhydrous dimethylformamide was stirred at room temperature for 30 minutes and 15 mL of anhydrous dichloromethane was added. The reaction solution was stirred at room temperature overnight and concentrated in vacuo. The residue was recrystallized from 2-propanol to give 1.43 g (95%) of 27d.

$^{13}$C NMR (67.80 MHz, CDCl$_3$) δ 15.15, 39.83, 52.85, 62.05, 64.75, 66.83–70.45 (PEG) 77.19, 111.95, 120.15, 127.58, 128.73, 129.38, 133.62, 141.35, 147.12, 151.91, 153.00.

Example 31

Synethesis of compound (27c)

DIEA (0.15 mL, 0.86 mmol) was added to a mixture of 1.0 g (0.025 mmol) of 6c and 60 mg (0.20 mmol) of melphalan in 15 mL of anhydrous dimethylformamide and the mixture was stirred at room temperature for 30 minutes. Anhydrous dichlormethane (5 mL) was added and the reaction solution was stirred at room temperature overnight and concentrated in vacuo. The residue was recrystallized form 2-propanol to give 0.85 g (85%) of 27e.

$^{13}$C NMR (67.80 MHz, CDCl$_3$) δ 15.06, 36.71, 39.63, 52.43, 54.60, 64.01, 66.77–70.43 (PEG) 111.01, 124.26, 127.44, 129.27, 129.73, 134.18, 144.03, 147.03, 151.83, 154.52, 171.68.

Example 32

Synthesis of (28b)

A mixture of 1.0 g (0.025 mmol) of 12a, 65 mg (0.11 mmol) of daunorubicin hydrochloride and 46 mg (0.38 mmol) of DMAP in 10 mL of dry dimethylformamide was stirred at room temperature for 18 hours. To this mixture was added 30 mL of ether. The precipitate was collected by filtration and washed with ether followed by crystallization from 2-propanol to yield 0.88 g (88% yield) of 28b. UV assay for this compound indicated the amount of daunorubicin present is 2.2%. In vitro and in vivo results for this compound are set forth in Table 1 below.

Example 33

Synthesis of (29a)

A mixture of 0.5 g (0.09 mmol) of 14a, 65 mg (0.11 mmol) of daunorubicin hydrochloride and 46 mg (0.38 mmol) of DMAP in 10 mL of dry dimethylformamide was stirred at room temperature for 18 hours. To this mixture was added 30 mL of ether. The precipitate was collected by filtration and washed with ether followed by crystallization from 2-propanol to yield 0.44 g (80% yield) of product.

$^{13}$C NMR (67.80 MHz, CDCl$_3$) δ 16.20, 23.99, 29.04, 32.29, 34.21, 46.55, 55.84, 58.12, 65.14, 68.14, 68.57, 68.76, 68.81, 69.31–73.37 (PEG), 75.78, 100.11, 110.21, 110.38, 117.93, 118.81, 119.00, 119.25, 119.77, 128.05, 128.48, 131.69, 133.57, 134.39, 134.99, 154.86, 155.53, 160.16, 167.46, 185.58, 185.77, 211.09.

Example 34

Synthesis of compound (29b)

Compound 29b was prepared in a similar manner to compound 29a using a 40 kDa PEG linker 14b in place of the 5 kDaPEG linker 14a. UV assay for this compound indicated the amount of daunorubicin present is 2.1%.

Example 35

Synthesis of (30b)

A mixture of 1.0 g (0.025 mmol) of 18a, 65 mg (0.11 mmol) of daunorubicin hydrochloride and 46 mg (0.38 mmol) of DMAP in 10 mL of dry dimethylformamide was stirred at room temperature for 18 hours. To this mixture was added 30 mL of ether. The precipitate was collected by filtration and washed with ether followed by crystallization from 2-propanol to yield 0.88 g (88% yield) of 28b. UV assay for this compound indicated the amount of daunorubicin present is 2.2%. In vitro and in vivo results for this compound are set forth in Table 1 below.

Example 36

Synthesis of compound (31a)

A mixture of 0.5 g (0.09 mmol) of 21a, 65 mg (0.11 mmol) of daunorubicin hydrochloride and 46 mg (0.38 mmol) of DMAP in 10 mL of dry dimethylformamide was stirred at room temperature for 18 hours. To this mixture is added 30 mL of ether. The precipitate was collected by filtration and washed with ether followed by crystallization from 2-propanol to yield 0.44 g (80% yield) of 31a.

Example 37

Synthesis of compound (31b)

Compound 31bwas prepared in a similar manner to compound 31ausing a 40 kDa PEG linker 21bin place of 5 kDa linker 21a. UV assay for this compound indicated the amount of daunorubicin present is 2.6%. In vitro and in vivo results for this compound are set forth in Table 1 below.

Example 38

Synthesis of compound (32a)

To a solution of 2 g (0.4 mmol) of 1aand 0.2 g (0.8 mmol) of N,N-disuccinimidyl carbonate in 25 mL of anhydrous methylene chloride was added 30 μL (0.4 mmol) of anhydrous pyridine at 0° C. under nitrogen atmosphere and the solution was stirred overnight at 4° C. The product was precipitated by the addition of 300 mL of ether. The solid obtained was recrystallized from methylene chloride/ether to give 1.6 g (80%) of the product 32C as a white solid.

$^{13}$C NMR (67.80 MHz, CDCl$_3$) δ 24.8, 58.3, 67.2–71.3 (PEG), 120.8, 129.2, 130.6, 150.9, 151.0, 152.6, 168.2.

Example 39

Synthesis of compound (32b)

Compound 32bwas prepared in a similar manner to 32astarting from 3a.

$^{13}$C NMR (67.80 MHz, CDCl$_3$) δ 25.0, 58.5, 67.8–71.8 (PEG), 121.4, 129.5, 130.7, 150.3, 151.1, 168.3, 168.4.

Example 40

Synthesis of compound (32c)

Compound 32cwas prepared in a similar manner to 32astarting from 5a.

$^{13}$C NMR (67.80 MHz, CDCl$_3$) δ 16.0, 25.0, 58.6, 67.8–71.8 (PEG), 128.6, 130.4, 130.7, 140.9, 151.2, 167.8, 168.3.

Example 41

Synthesis of compound (32d)

Compound 32dwas prepared in a similar manner to 32astarting from 5d.

$^{13}$C NMR (67.80 MHz, CDCl$_3$) δ 15.2, 24.6, 58.1, 67.0–71.2 (PEG), 128.1, 130.0, 130.4, 148.0, 150.8, 151.8, 168.1.

Example 42

Conjugation of compound 2aor 32ato (L)-asparaginase; synthesis of compound (33):

PEG linker 2aor 32a(450 mg, 0.084 mmol, 317 eq) was added to native (L)-asparaginase (37.5 mg, 416 μL, 0.00027 mmol) in 3 mL of sodium phosphate buffer (0.1 M, pH 7.8) with gentle stirring. The solution was stirred at 30° C. for 30 minutes. A GPC column (Zorbax GF-450) was used to monitor PEG conjugation: The PEG-Asp conjugate had a retention time of 8.5 min. At the end of the reaction (as evidenced by the absence of native enzyme), the mixture was diluted with 12 mL of formulation buffer (0.05 M sodium phosphate, 0.85% sodium chloride, pH 7.3) and diafiltered with a Centriprep concentrator (Amicon) having a molecular weight cut-off of 50,000 daltons to remove the unreacted PEG. Dialfiltration was continued as needed at 4° C. until no more free PEG was detected by mixing equal amount of filtrate and 0.1% PMA (polymethacrylic acid in 0.1 M HCl).

Compound 33 was not stable in basic buffer solution for prolonged periods of time, therefore the solution was lyophilized and 33 stored in the freezer (−20° C.). After 15 days of storage in this manner, GPC analysis indicated less than 0.8% decomposition. The specific activity of freshly prepared 33 was found to be 137 IU/mg (native asparaginase= 217 IU/mg). Protein modification fo asparaginase with SS-PEG (a permanent linker) using a procedure corresponding to that described in the aforementioned U.S. Pat. No. 4,179,337 gave a similar activity of 120 IU/mg. A TNBS assay was used to calculate the percentage modification of the protein, and the Biuret assay was used to check the protein concentration.

Example 43

Kinetics of hydrolysis of PEG conjugate of (L)-asparaginase (33) in rat plasma and buffer The rate of hydrolysis of compound 33 in rat plasma was measured using a GPC column (Zorbax GF-450) and was found to have a half life of 82 minutes. In vitro kinetics were done and the half life was determined to be 10±2 hours in phosphate buffer (pH 7.4).

Example 44

Synthesis of (34), a protein hybrid; conjugation of (33) with SS-PEG (a permanent linker PEG linker 2a(393 mg, 0.073 mmol, 70 eq) was reacted with native (L)-asparaginase (150 mg, 1.664 mL. 0.00106 mmol) in 30 mL of sodium phosphate buffer (0.1 M, pH 7.8) as described in Example 36 at 30° C. for 15 minutes to provide a solution of 33, followed by the addition of SS-PEG (1.272 g, 0.245 mmol, 230 eq). The reaction solution was stirred for another 15 minutes. The pH of the reaction mixture was maintained at 7.8 with 0.5 M sodium hydroxide. The reaction was diluted with 30 mL of sterile water and diafiltered using a Centriprep concentrator (Amicon) Having a molecular weight cut-off of 50,000 daltons to remove any unreacted PEG. Dialfiltration was continued as needed at 4° C. until no more free PEG was detected by mixing equal amount of filtrate and 0.1% PMA (polymethacrylic acid in 0.1 M HCl). A GPC column (Zorbax GF-450) was used to follow the course of the reaction. The final solution of 34 was lyophilized and stored in the freezer.

Example 45

Demonstration of selective removal of reversible PEG linker (2a) from the hybrid (34); Generation of a permanently modified asparaginase, compound (35)

100 mg of 34 is dissolved in 30 mL of pH 7.8 phosphate buffer and stirred at 30° C. overnight. This solution is diluted with 30 mL of sterile water, and diafiltered with a Centriprep concentrator (Amicon) having a molecular weight cut off of 50,000 Daltons to remove free PEG which was formed by selective cleavage of the conjugates formed form the PEG-2alinker. The solution now contains only SS-PEG conjugated asparaginase (35). Thus, the reversible linker is hydrolyzed, leaving only the relatively permanently bonded PEG attached to the asparaginase.

Example 46

Synthesis of compound (36)

A mixture of 6 g (0.15 mmol) of 40 kDa PEG dithiazolidine thione amide, 150.9 mg (0.45 mmol) of tripeptide Gly-Phe-Leu, and 76 mg (0.6 mmol) of DIEA in anhydrous methylene chloride was stirred for 18 hours. The reaction mixture was washed with 0.1 N HCl (2×5 mL), followed by water (5 mL) and dried over anhydrous magnesium sulfate. The solvent was removed under reduced pressure to yield a solid that was recrystallized form 2-propanol to give 4.9 g (80%) of 36.

$^{13}$C NMR (67.80 MHz, CDCl$_3$) δ 21.41, 22.17, 24.21, 36.94, 40.66, 42.31, 50.42, 53.86, 70.64–72.22 (PEG) 126.14, 127.87, 128.73, 136.31, 168.42, 169.91, 170.28, 172.21.

Example 47

Synthesis of compound (37)

A solution of 1.1 g (4.04 mmol) of t-Boc-glycine N-hydroxysuccinimide ester and 1 g (8.12 mmol) of 4-aminobenzyl alcohol in 15 mL of methylene chloride was stirred at room temperature for 18 hours. The reaction mixture was filtered to remove the precipitated solid (byproduct NHS) and the filtrate was washed with 0.1 N HCl (2×5 mL), followed by water (5 mL) and dried. The solvent was removed under reduced pressure to yield a residue that was triturated with ether to give 900 mg (75%) of the pure t-Boc-glycine amide of 4-aminobenzyl alcohol.

$^{13}$C NMR (67.80 MHz, CDCl$_3$) δ 28.27, 44.87, 64.45, 80.50, 120.19, 127.66, 136.73, 137.01, 156.55, 168.24.

TFA (2.5 mL was added to a solution of 500 mg (1.78 mmol) of t-Boc-glycine amide of 4-aminobenzyl alcohol in methylene chloride (5 mL), and the solution was stirred for 30 minutes at room temperature. Anhydrous diethylether (50 mL) was added to precipitate the solid that was filtered, washed thoroughly with ether until all the TFA is washed, and dried to give 300 mg (60%) of the 37 as a TFA salt.

$^{13}$C NMR (67.80 MHz, DMSO-d$_6$) δ 41.01, 62.58, 119.01, 127.22, 136.79, 138.13, 164.62.

Example 48

Synthesis of compound (38)

To a solution of 1 g (0.025 mmol) of 36 and Z30 mg (0.10 mmol) of 37 in 10 mL of methylene chloride at 0° C. is added 19.2 mg (0.1 mmol) of EDC and 25 mg (0.2 mmol) of DMAP and the mixture is stirred for 3 hours at 0° C., followed by 18 h at room temperature. The solvent is removed under reduced pressure and the solid obtained is recrystallized from 2-propanol to give the product 38.

Example 49

Synthesis of compound (39)

A solution of 3.0 g (0.075 mmol) of 38 in 140 mL of toluene is azeotroped for 2 hours while removing 40 mL of toluene/water. The reaction mixture is cooled to 30° C. followed by the addition of 0.06 g (0.3 mmol) of PNP-Cl and 0.04 g (0.3 mmol) of DIEA. The reaction mixture is stirred for 18 hours at 50–55° C. followed by cooling and removal of the solvent by distillation in vacuo. The residue is crystallized from 20% methylene chloride in ethyl ether to yield 39.

Example 50

Synthesis of compound (40)

A mixture of 0.8 g (0.02 mmol) of 39, 45 mg (0.1 mmol) of daunorubicin hydrochloride, and 32 mg (0.26 mmol) of DMAP in 10 mL of dry dimethylformamide is stirred at room temperature for 18 hours. To this mixture is added 30 mL of ether. The precipitate is collected by filtration and washed with ether followed by crystallization from 2-propanol to yield the product 40.

Example 51

Synthesis of compound (42)

A solution of 4.0 g (0.1 mmol) of (di-SC)-PEG 40 kDa and 0.1 g (0.8 mmol) of 2-aminobenzyl alcohol in 30 mL of dry methylene chloride was refluxed overnight. The solvent was removed by distillation in vacuo, and the residue was crystallized form 2-propanol to yield the product 41.

A solution of 3.0 g (0.07 mmol) of 41 in 140 mL of toluene is azeotroped for 2 hours while removing 40 mL of toluene/water. The reaction mixture is cooled to 30° C. followed by the addition of 0.06 g (0.3 mmol) of PNP-Cl and 0.04 g (0.3 mmol) of DIEA. This mixture is stirred for 18 hours at 50–55 ° C. followed by cooling and removal of the solvent by distillation in vacuo. The residue is crystallized from 20% methylene chloride in ether to yield the product 42.

Example 52

Synthesis of compound (44)

A solution of 4.0 g (0.1 mmol) of 40 kDa PEG isocyanate, 0.1 g, (0.8 mmol) of 2-hydroxybenzaldehyde, and 0.1 g (0.8 mmol) of DMAP in 50 mL of dry methylene chloride is refluxed for 18 hours. The solvent is removed form the reaction mixture by distillation in vacuo followed by crystallization of the residue from 2-propanol to yield the aldehyde. NaBH$_4$ reduction of the aldehyde product in methanol gives the corresponding benzyl alcohol 43.

A solution of 3.0 g (0.07 mmol) of 43 in 140 mL of toluene is azeotroped for 2 hours while removing 40 mL of toluene/water. The reaction mixture is cooled to 30° C. followed by the addition of 0.06 g (0.3 mmol) of PNP-Cl and 0.04 g (0.3 mmol) of DIEA. This mixture is stirred for 18 hours. at 50–55° C. followed by cooling and removal of the solvent by distillation in vacuo. The residue is crystallized form 20% methylene chloride in ether to yield the product 44.

Example 53

Synthesis of compound (45)

A mixture of 0.8 g (0.02 mmol) of 42, 45 mg (0.1 mmol) of daunorubicin hydrochloride and 32 mg (0.26 mmol) of DMAP in 10 mL of dry dimethylformamide is stirred at room temperature for 18 hours. To this mixture is added 30 mL of ether. The precipitate is collected by filtration and washed with ether followed by crystallization from 2-propanol to yield the product 45.

Example 54

Synthesis of compound (46)

A mixture of 0.8 g (0.02 mmol) of 44, 45 mg (0.1 mmol) of daunorubicin hydrochloride and 32 mg (0.26 mmol) of DMAP in 10 mL of dry dimethylformamide is stirred at room temperature for 18 hours. To this mixture is added 30 mL of ether. The precipitate is collected by filtration and washed with ether followed by crystallization from 2-propanol to yield the product 46.

Example 55

Synthesis of compound (47)

A mixture of 160 mg (4.1 mmol) of sodium borohydride and 0.2 g (1.4 mmol) of nitrofuranylmethanol in 20 mL of 2-propanol is stirred at room temperature for 16 hours and the suspension was filtered through Celite. The filtrate is concentrated in vacuo to give a crude product 47 which is used for next step without further purification.

Example 56

Synthesis of compound (48)

A solution of 4.0 g (0.1 mmol) of (di-SC)-PEG 40 kDa and 0.09 g (0.8 mmol) of 47 in 30 mL of dry methylene chloride is refluxed overnight. The solvent is removed by distillation in vacuo, and the residue is recrystallized from 2-propanol to yield the product 48.

Example 57

Synthesis of compound 49)

A solution of 3.0 g (0.07 mmol) of 48 in 140 mL of toluene is azeotroped for 2 hours while removing 40 mL of toluene/water. The reaction mixture is cooled to 30° C. followed by the addition of 0.06 g (0.3 mmol) of PNP-Cl and 0.04 g (0.3 mmol) of DIEA. This mixture is stirred for 18 hours at 50–55° C. followed by cooling and removal of the solvent by distillation in vacuo. The residue is crystallized form 20% methylene chloride in ether to yield the product 49.

Example 58

Synthesis of compound (50)

A mixture of 0.8 g (0.02 mmol) of 49, 45 mg (0.1 mmol) of daunorubicin hydrochloride and 32 mg (0.26 mmol) of DMAP in 10 mL of dry dimethylformamide is stirred at room temperature for 18 hours. To this mixture is added 30 mL of ether. The precipitate is collected by filtration and washed with ether followed by crystallization from 2-propanol to yield the product

TABLE 1

In Vitro and In Vivo Results of PEG 40kDa-Daunorubicin Prodrugs

| Compound # | $t_{½}$ (h) pH 7.4 | $t_{½}$ (h) rat plasma | $IC_{50}$ (nM) P388/O | M109[a] % T/C | SKOV3[b] % T/C |
|---|---|---|---|---|---|
| Daunorubicin HCl | — | — | 2.3 | 68.0[c] | 35.2 |
| Esters | | | | | |
| 24b | >24 | 0.4 | 8 | 92.8 | — |
| 27b | >48 | 1.9 | 55 | 90.3 | — |
| 30b | >48 | 1.3 | 18 | 89.6 | — |
| Carbamates | | | | | |
| 31b | >48 | 4.1 | 15 | 84.1 | 7.6 |
| 28b | >48 | >24 | 415 | 75.3 | 51.7 | a: 3 mg/kg/dose of active daunorubicin was given i.p. in balb/c mice bearing S. C. Madison 109 Lung Carcinoma at 1 & 4 days after inoculation. The median tumor volume of treatment and control groups were measured and compared when the control group's median tumor volume reached approximately 2000 mm$^3$.

b: 3 mg/kg/dose of active daunorubicin was administered intravenously in nude mice bearing a human ovarian carcinoma xenografts at 1, 5 & 9 days after inoculation. The median tumor volume of treatment and control groups were measured and compared when the control group's median tumor volume reached approximately 1000 mm$^3$.

c Willaim C. Rose. Evaluation of Madison 109 Lung Carcinoma as a Model for Screening Antitumor Drugs.Cancer Treatment Reports, 1981, 65, 229.

The various publications, patents, patent applications and published applications mentioned in this application are hereby incorporated by reference herein.

While there have been described what are presently believed to be the preferred embodiments of the invention, those skilled in the art will realize that changes and modifications may be made without departing from the spirit of the invention. It is intended to claim all such changes and modifications as fall within the true scope of the invention.

We claim:

1. A compound comprising the formula:

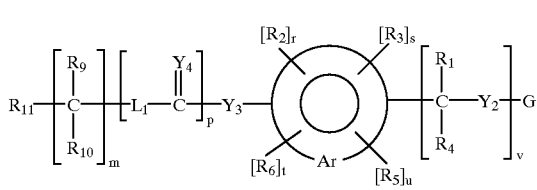

(I)

wherein:
  $L_1$ is a bifunctional linking moiety;
  G is H or

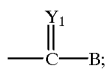

where
  B is H, a leaving group, a residue of an amine-containing moiety, or a residue of a hydroxyl-containing moiety;
  $Y_{1-4}$ are independently O, S, or $NR_{12}$;
  $R_1$, $R_4$, $R_9$, $R_{10}$, and $R_{12}$, are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, and substituted $C_{1-6}$ heteroalkyls;
  $R_2$, $R_3$, $R_5$ and $R_6$ are independently selected from the group consisting of hydrogen, $C_{1-6}$ alkyls, $C_{1-6}$ alkoxy, phenoxy, $C_{1-8}$ heteroalkyls, $C_{1-8}$ heteroalkoxy, substituted $C_{1-6}$ alkyls, $C_{3-8}$ cycloalkyls, $C_{3-8}$ substituted cycloalkyls, aryls, substituted aryls, aralkyls, halo-, nitro-, cyano-, carboxy-, $C_{1-6}$ carboxyalkyls and $C_{1-6}$ alkyl carbonyls;
  Ar is a moiety which when included in Formula (I) forms a multi-substituted aromatic hydrocarbon or a multi-substituted heterocyclic group;
  (m), (r), (s), (t), (u) and (v) are independently zero or one;
  (p) is zero or a positive integer; and
  $R_{11}$ is a substantially non-antigenic polymer,
except that
  (1) G is not H when (v) is 0;
  (2) $R_{11}$ is not $-C(=Y)-(CH_2)_n-O-(CH_2CH_2O)_x-CH_3$ when m=0, p=0 and $Y_3$=NH and
  (3) $R_{11}$ is not $CH_3-O-(CH_2CH_2O)_x-CH_2)_n$ when m=0, p=1, $L_1$=OCH$_2$, $Y_4$=O and $Y_3$=NH wherein (n) is zero or a positive integer; Y is O, S or $NR_{12}$; and (x) represents the degree of polymerization.

2. The compound of claim 1, wherein:
  $L_1$ is selected from the group consisting of

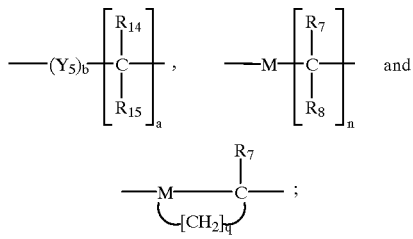

and

wherein:
  M is X or Q; where
    X is an electron withdrawing group;
    Q is a moiety containing a free electron pair positioned three to six atoms from $$\overset{Y_4}{\underset{}{\overset{\|}{C}}};$$

(a) and (n) are independently zero or a positive integer;
  (b) is zero or one;
  (q) is three or four;
  $R_7$, $R_8$, $R_{14}$, and $R_{15}$ are independently selected from the group which defines $R_9$; and
  $Y_5$ is O, S, or $NR_{12}$.

3. The compound of claim 1, wherein Ar is selected from the group consisting of:

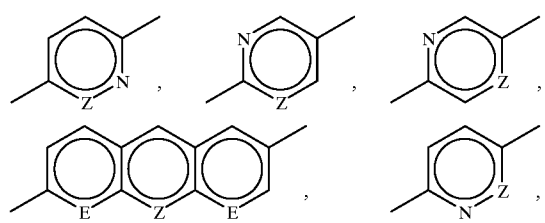

wherein J is O, S, or $NR_{13}$, E and Z are independently $CR_{13}$ or $NR_{13}$; and $R_{13}$ is independently selected from the same group as that which defines $R_9$.

4. A compound of claim 1, having the formula

5. The compound of claim 1, wherein $R_1$, $R_4$, $R_9$ and $R_{10}$ are all H.

6. The compound of claim 1, having the formula:

7. The compound of claim 2, wherein comprises an amino acid residue.

8. The compound of claim 7, wherein said amino acid residue is selected from the group consisting of naturally occurring and non-naturally occurring amino acid residues.

9. The compound of claim 1, wherein (p) is one.

10. The compound of claim 1, wherein $R_{11}$ includes a capping group A.

11. The compound of claim 10, wherein A is selected from the group consisting of hydrogen, $CO_2H$, $C_{1-6}$ alkyl moieties, dialkyl acyl urea alkyls and (II)

wherein G' is the same as G or another member of the group defined as G.

12. The compound of claim 2, wherein X is selected from the group consisting of O, $NR_{12}$, S, SO and $SO_2$.

13. The compound of claim 12, wherein X is selected from the group consisting of O and $NR_{12}$.

14. The compound of claim 2, wherein Q is selected from the group consisting of $C_{2-4}$ alkyls, cycloalkyls, aryls, and aralkyl groups substituted with a member of the group consisting of NH, O, S, —$CH_2$-C(O)-N(H)—, and ortho-substituted phenyls.

15. The compound of claim 2, wherein (n) is 1 or 2.

16. The compound of claim 1, wherein (m) is 0.

17. The compound of claim 1, wherein $Y_{1-4}$ are O.

18. The compound of claim 1, wherein $R_{11}$ comprises a polyalkylene oxide.

19. The compound of claim 18, wherein said polyalkylene oxide comprises polyethylene glycol.

20. The compound of claim 1 wherein said polymer has a number average molecular weight of from about 2,000 to about 100,000 daltons.

21. The compound of claim 1, wherein said polymer has a number average molecular weight of from about 5,000 to about 40,000 daltons.

22. The compound of claim 1, wherein $R_{11}$ is selected from the group consisting of —C(=Y)-(CH$_2$)$_n$-O-(CH$_2$CH$_2$O)$_x$-A, —C(=Y)-Y-(CH$_2$)$_n$-O-(CH$_2$CH$_2$O)$_x$-A and —C(=Y)-NR$_{12}$-(CH$_2$)$_n$-O-(CH$_2$CH$_2$O)$_x$-A, where
(n) is zero or a positive integer;
Y is O, S or NR$_{12}$;
A is a capping group; and
(x) represents the degree of polymerization.

23. The compound of claim 1 wherein B is a leaving group selected from the group consisting of N-hydroxybenzotriazolyl, halogen, N-hydroxyphthalimidyl, p-nitrophenoxy, imidazolyl, N-hydroxysuccinimidyl, thiazolidinyl thioine, and an acid activating group.

24. The compound of claim 1 wherein B is a residue of a hydroxyl-containing compound.

25. The compound of claim 1, wherein B is a residue of an amine containing compound.

26. The compound of claim 1, wherein B includes a second polymeric transport system.

27. The compound of claim 4 wherein:
$L_1$ is

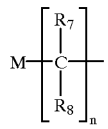

M is X or Q;
X is an electron withdrawing group;
Q is a moiety containing a free electron pair positioned three to six atoms from $Y_3$;
$R_7$ and $R_8$, are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, and substituted $C_{1-6}$ heteroalkyls;
(n) is zero or a positive integer;
r, s, t, u, p and v are all equal to 1; and
G is

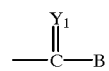

except that $R_2$, $R_3$, $R_5$ and $R_6$ are not all H when (m) and (n) are both zero.

28. The compound of claim 27, wherein $R_2$ and $R_6$ are $C_{1-6}$ alkyls.

29. The compound of claim 27, wherein $R_2$ and $R_6$ are methyl.

30. The compound of claim 27, wherein $R_2$ and $R_6$ are independently $C_{1-6}$.

31. The compound of claim 27, wherein $R_2$ and $R_6$ are methoxy.

32. The compound of claim 27, wherein $R_3$ and $R_5$ are hydrogen.

33. The compound of claim 27, wherein $R_1$ and $R_4$ are independently selected from the group consisting of hydrogen, CH$_3$ and CH$_2$CH$_3$.

34. The compound of claim 27, wherein said substituted $C_{1-6}$ alkyl is selected from the group consisting of carboxyalkyls, aminoalkyls, dialkylaminos, hydroxyalkyls and mercaptoalkyls.

35. The compound of claim 27, wherein X is selected from the group consisting of O, NR$_{12}$, S, SO and SO$_2$.

36. The compound of claim 35, wherein X is selected from the group consisting of O and NR$_{12}$.

37. The compound of claim 27, wherein Q is selected from the group consisting of $C_{2-4}$ alkyls, cycloalkyls, aryls, and aralkyl groups, and Q is substituted with a member of the group consisting of NH, NR$_{12}$, O, S, —CH$_2$-CH(O)-N(H)—, and ortho-substituted phenyls.

38. The compound of claim 27, wherein (n) is an integer from 1 to about 12.

39. The compound of claim 38, wherein (n) is 1 or 2.

40. The compound of claim 27, wherein B is a residue of a member of the group consisting of anthracyclins, daunorubicin, doxorubicin, p-hydroxyaniline mustard, cytosine arabinoside and gemcitabine.

41. The compound of claim 27, wherein B is a residue of an amine containing compound selected from the group consisting of cardiovascular agents, anti-neoplastics, anti-infectives, anti-fungals, anti-anxiety agents, gastrointestinal agents, central nervous system-activating agents, analgesics, fertility agents, contraceptive agents, anti-inflammatory agents, steroidal agents, anti-urecemic agents, vasodilating agents, and vasoconstricting agents.

42. The compound of claim 26, wherein B includes an attachment moiety for said second polymeric transport system selected from the group consisting of alpha amino, epsilon amino, histidine nitrogen, carboxyl, reactive carbonyl, mercapto, sulfhydryl and hydroxyl.

43. The compound of claim 42, wherein B is a member of the group consisting of proteins, polypeptides, peptides and enzymes.

44. The compound of claim 43, wherein B is a cytokine or an interferon.

45. The compound of claim 44, wherein said cytokine is an interleukin.

46. The compound of claim 45, wherein said interleukin is selected from the group consisting of IL-1, IL-2, IL-3, IL-4, IL-5, IL-6, IL-7, IL-8, IL-9, IL-10, IL-11, IL-12 and IL-13.

47. The compound of claim 44, wherein said interferon is selected from the group consisting of α-interferons, β-interferons and γ-interferons.

48. The compound of claim 1, wherein v=1.

49. The compound of claim 1, wherein (p) is four and

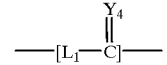

comprises Gly-Phe-Leu-Gly (SEQ ID NO:1).

50. A compound of claim 1, selected from the group consisting of:

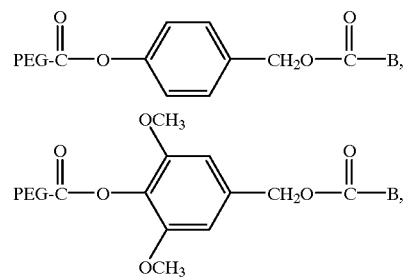

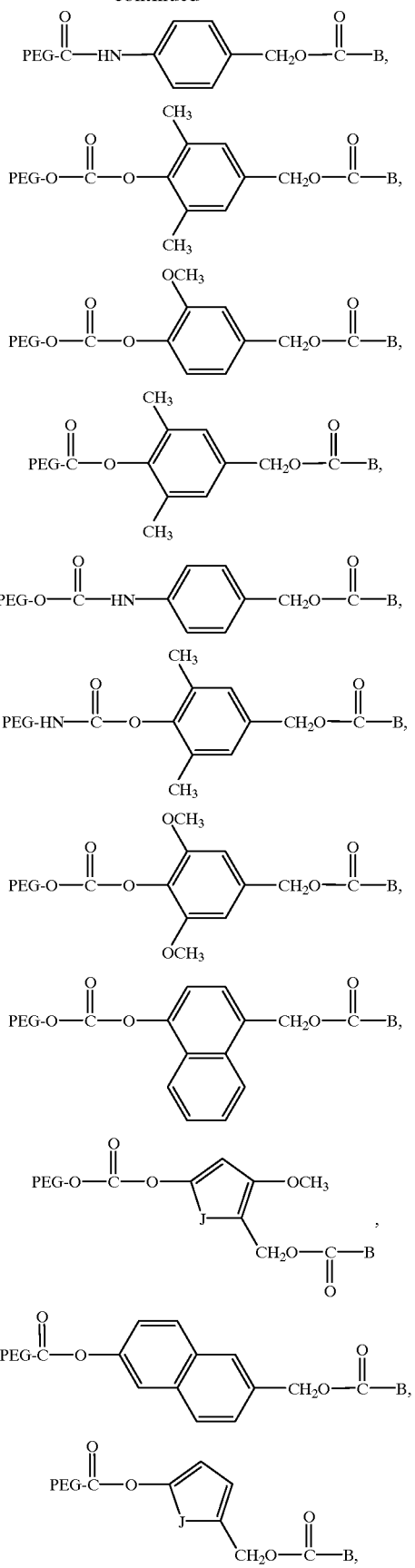
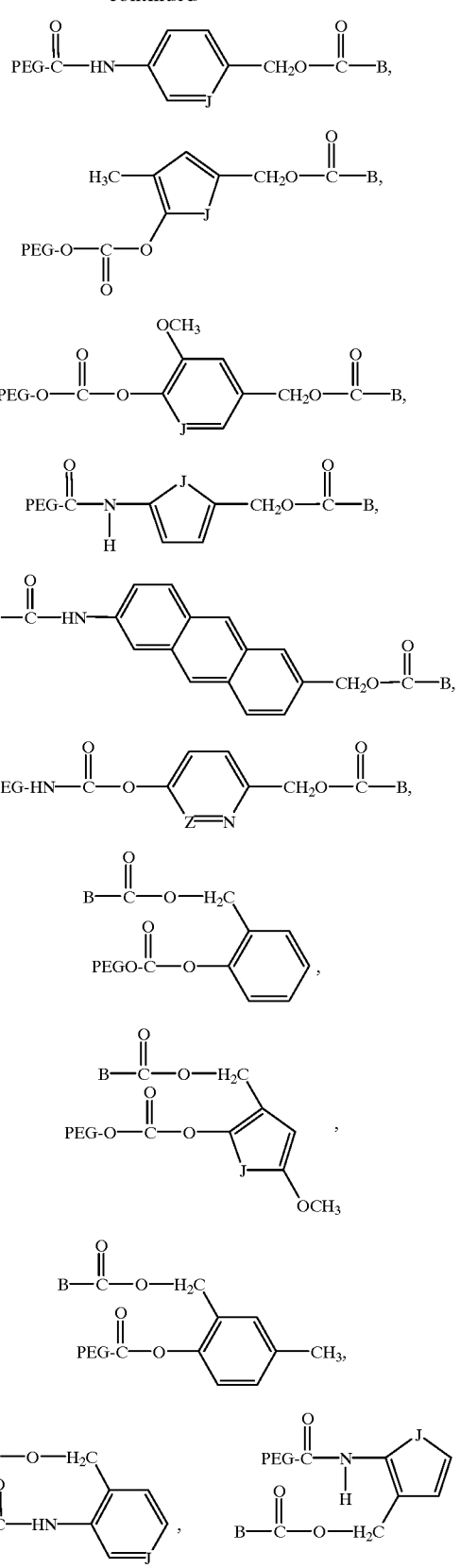

-continued

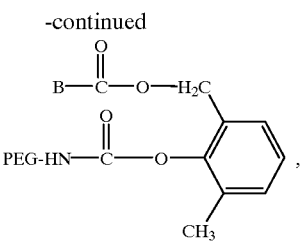

wherein J is O, S, or $NR_{13}$, E and Z are independently $CR_{13}$ or $NR_{13}$, and $R_{13}$ is independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, and substituted $C_{1-6}$ heteroalkyls.

51. A composition comprising a compound of the formula:

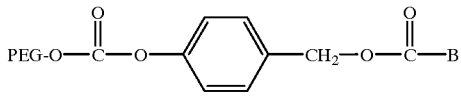

wherein B is a leaving group or a residue of an amine-containing target moiety.

52. A method of treating a mammal with prodrugs, comprising:

administering to a mammal in need of such treatment an effective amount of a pharmaceutically acceptable composition comprising the compound of claim 1, wherein B is a residue of an amine-containing or hydroxyl-containing biologically active moiety.

53. A method for preparing a prodrug transport form comprising:

a. providing an intermediate compound (III)

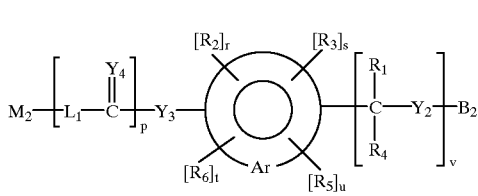

wherein $M_2$ is a cleavable or reversible protecting group;
$L_1$ is a bifunctional linking moiety;
$B_2$ is selected from the group consisting of H, OH,

and leaving groups;
$Y_{1-4}$ are independently O, S, or $NR_{12}$;
(r), (s), (t), (u) and (v) are independently zero or one;
(p) is zero or a positive integer;
$R_1$, $R_4$, and $R_{12}$, are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, and substituted $C_{1-6}$ heteroalkyls;

$R_2$, $R_3$, $R_5$ and $R_6$ are independently selected from the group consisting of hydrogen, $C_{1-6}$ alkyls, $C_{1-6}$ alkoxy, phenoxy, $C_{1-8}$ heteroalkyls, $C_{1-8}$ heteroalkoxy, substituted $C_{1-6}$ alkyls, $C_{3-8}$ cycloalkyls, $C_{3-8}$ substituted cycloalkyls, aryls, substituted aryls, aralkyls, halo-, nitro-, cyano-, carboxy-, $C_{1-6}$ carboxyalkyls and $C_{1-6}$ alkyl carbonyls; and Ar is a moiety which forms a multi-substituted aromatic hydrocarbon or a multi-substituted heterocyclic group; except that G is not H when (v) is 0;

b. removing the protecting group;

c. reacting the resultant unprotected intermediate compound with an activated polymer capable of reacting with $L_1$ to form an intermediate activated double prodrug transport form; and d. reacting the intermediate activated double prodrug transport form with an activating moiety donor.

54. The method of claim 53, further comprising the step of:

e. reacting the prodrug transport form of step d with an amine-containing or hydroxyl-containing compound residue to form a conjugate.

55. The method of claim 53 further comprising reacting the compound of formula (I) with an activating polymer to form a hybrid transport system.

56. A method for preparing a prodrug transport form comprising:

a. providing an intermediate compound (III)

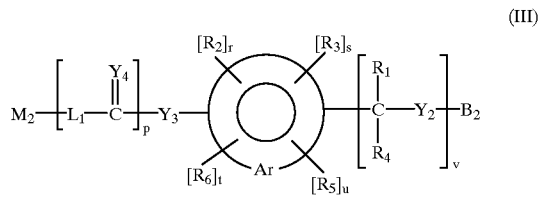

wherein $M_2$ is a cleavable or reversible protecting group;
$L_1$ is a bifunctional linking moiety;
$B_2$ is selected from the group consisting of H, OH,

and leaving groups;
$Y_{1-4}$ are independently O, S, or $NR_{12}$;
(r), (s), (t), (u) and (v) are independently zero or one;
(p) is zero or a positive integer;
$R_1$, $R_4$, and $R_{12}$, are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, and substituted $C_{1-6}$ heteroalkyls;

$R_2$, $R_3$, $R_5$ and $R_6$ are independently selected from the group consisting of hydrogen, $C_{1-6}$ alkyls, $C_{1-6}$ alkoxy, phenoxy, $C_{1-8}$ heteroalkyls, $C_{1-8}$ heteroalkoxy, substituted $C_{1-6}$ alkyls, $C_{3-8}$ cycloalkyls, $C_{3-8}$ substituted cycloalkyls, aryls, substituted aryls, aralkyls, halo-, nitro-, cyano-, carboxy-, $C_{1-6}$ carboxyalkyls and $C_{1-6}$ alkyl carbonyls; and Ar is a moiety which forms a multi-substituted aromatic hydrocarbon or a multi-substituted heterocyclic group when compound III is reacted with an activating moiety donor except that G is not H when (v) is 0;

b. reacting intermediate compound III with an activating moiety donor and then reacting the resultant activated product with an amine-containing or hydroxyl-containing compound;

c. removing the protecting group from the last product of step b, to form an unprotected intermediate; and d. reacting the unprotected intermediate of step c with an activated polymer to form the prodrug transport form.

* * * * *

UNITED STATES PATENT AND TRADEMARK OFFICE
CERTIFICATE OF CORRECTION

PATENT NO. : 6,180,095 B1
DATED : January 30, 2001
INVENTOR(S) : Greenwald, Richard et al.

It is certified that error appears in the above-identified patent and that said Letters Patent is hereby corrected as shown below:

<u>Title page,</u>
Item [75], entitled "Inventors": please delete "Richard B. Greenwald, Somerset; Annapurna Pendri, Matawan; Yun H. Choe, Piscataway, all of NJ (US)" and insert -- Richard B. Greenwald, Somerset; Annapurna Pendri, Matawan; Yun H. Choe, Piscataway, all of NJ (US) and Samuel Zalipsky, Redwood City, CA (US) --

Signed and Sealed this

Twenty-first Day of May, 2002

*Attest:*

JAMES E. ROGAN
*Attesting Officer*     *Director of the United States Patent and Trademark Office*

SEQUENCE LISTING

<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence:Peptide linker.

<400> SEQUENCE: 1

Gly Phe Leu Gly